(12) United States Patent
Marom et al.

(10) Patent No.: US 9,096,574 B2
(45) Date of Patent: Aug. 4, 2015

(54) POLYMORPHS OF PERAMPANEL

(71) Applicant: MAPI PHARMA LTD., Ness Ziona (IL)

(72) Inventors: Ehud Marom, Kfar Saba (IL); Shai Rubnov, Tel Aviv (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days.

(21) Appl. No.: 14/370,615

(22) PCT Filed: Jan. 1, 2013

(86) PCT No.: PCT/IL2013/050001
§ 371 (c)(1),
(2) Date: Jul. 3, 2014

(87) PCT Pub. No.: WO2013/102897
PCT Pub. Date: Jul. 11, 2013

(65) Prior Publication Data
US 2014/0371273 A1    Dec. 18, 2014

Related U.S. Application Data

(60) Provisional application No. 61/582,501, filed on Jan. 3, 2012.

(51) Int. Cl.
| C07D 213/64 | (2006.01) |
| A61K 31/444 | (2006.01) |
| C07D 401/04 | (2006.01) |

(52) U.S. Cl.
CPC ............ *C07D 401/04* (2013.01); *A61K 31/444* (2013.01); *C07D 213/64* (2013.01)

(58) Field of Classification Search
CPC ... C07D 401/04; C07D 213/64; A61K 31/444
USPC .......................................... 546/257; 514/334
See application file for complete search history.

(56) References Cited

U.S. PATENT DOCUMENTS

| 7,524,967 B2 | 4/2009 | Koyakumaru et al. |
| 7,563,811 B2 | 7/2009 | Nagato et al. |
| 7,718,807 B2 | 5/2010 | Nagato et al. |
| 7,803,818 B2 | 9/2010 | Omae et al. |
| 7,939,549 B2 | 5/2011 | Nagato et al. |
| 2008/0312284 A1 | 12/2008 | Omae et al. |
| 2009/0088574 A1 | 4/2009 | Urawa et al. |
| 2010/0324297 A1 | 12/2010 | Arimoto et al. |

FOREIGN PATENT DOCUMENTS

| EP | 1300396 A1 | 4/2003 |
| EP | 1764361 A1 | 3/2007 |
| WO | 03/047577 A2 | 6/2003 |

OTHER PUBLICATIONS

Brittain HG (1999) "Polymorphism in Pharmaceutical Solids", Marcel Dekker, Inc., chapter 5, parts B and C, pp. 188-195.

*Primary Examiner* — Patricia L Morris
(74) *Attorney, Agent, or Firm* — Rothwell, Figg, Ernst & Manbeck, P.C.

(57) ABSTRACT

The present invention provides novel crystalline forms of perampanel, pharmaceutical compositions comprising same, methods for their preparation and uses thereof for treating seizures and epilepsy.

7 Claims, 22 Drawing Sheets

POLYMORPHS OF PERAMPANEL

CROSS REFERENCE TO RELATED APPLICATIONS

The present application is a 35 U.S.C. §371 National Phase Entry application from PCT/IL2013/050001, filed Jan. 1, 2013, and designating the United States, which claims the benefit of U.S. Provisional Application No. 61/582,501 filed on Jan. 3, 2012, which are incorporated herein in their entireties.

FIELD OF THE INVENTION

The present invention relates to novel crystalline polymorphic forms of perampanel, pharmaceutical compositions comprising same, and uses thereof in the treatment of epilepsy and seizures.

BACKGROUND OF THE INVENTION

Perampanel (FYCOMPA™) is a first-in-class, highly selective non-competitive AMPA-type glutamate receptor antagonist indicated for adjunctive therapy for the treatment of partial-onset seizures with or without secondarily generalized seizures in patients with epilepsy aged 12 years and older. Perampanel is chemically designated 5'-(2-cyanophenyl)-1'-phenyl-2,3'-bipyridinyl-6'(1'H)-one or 3-(2-cyanophenyl)-5-(2-pyridyl)-1-phenyl-1,2-dihydropyridin-2-one, and is represented by the following chemical structure:

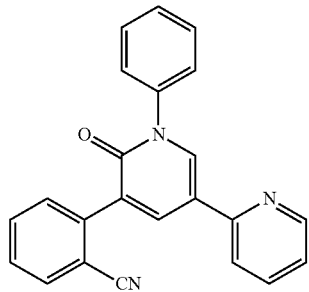 [SMILES: N#Cc1ccccc1-c1cc(-c2ccccn2)cn(-c2ccccc2)c1=O]

Perampanel and other 1,2-dihydropyridine compounds which possess antagonistic action against AMPA receptor and/or inhibitory action against kainate receptor are described in WO 01/96308. Example 7 in WO 01/96308 discloses a process for producing perampanel by reacting 3-(2-cyanophenyl)-5-(2-pyridyl)-2(1H)-pyridone with phenyl boronic acid, copper acetate and triethylamine in methylene chloride, followed by addition of concentrated aqueous ammonia, water and ethyl acetate. After work-up (phase separation, washing the organic phase and drying over magnesium sulfate), the solvent was concentrated in vacuo and the residue was purified by a silica gel column chromatography (ethyl acetate:hexane=1:2) to give the title product as pale yellow powder. There is no disclosure regarding the polymorphic nature of the product.

A new crystalline or amorphous form of a compound may possess physical properties that differ from, and are advantageous over, those of other crystalline or amorphous forms. These include, packing properties such as molar volume, density and hygroscopicity; thermodynamic properties such as melting temperature, vapor pressure and solubility; kinetic properties such as dissolution rate and stability under various storage conditions; surface properties such as surface area, wettability, interfacial tension and shape; mechanical properties such as hardness, tensile strength, compactibility, handling, flow and blend; and filtration properties. Variations in any one of these properties may affect the chemical and pharmaceutical processing of a compound as well as its bioavailability and may often render the new form advantageous for pharmaceutical and medical use.

EP 1764361 (US 2010/324297) discloses three anhydrous crystalline forms of perampanel, designated Form I, Form III and Form V and a hydrate form of perampanel. Anhydrous Form I is prepared in accordance with Example D1 by dissolving perampanel in ethyl acetate (EtOAc) under reflux, cooling the solution, seeding with anhydrous perampanel crystals, continued cooling and collecting the precipitated crystals. Anhydrous Form V is prepared in accordance with Example C1, by dissolving perampanel in acetone, heating to reflux and concentrating the solution to solidification, dissolving the solids in acetone-water, refluxing then cooling and collecting the precipitate. The hydrate form is prepared in accordance with Example B1 by dissolving perampanel in acetone-water, heating, cooling the solution, seeding with perampanel hydrate crystals, continued cooling and collecting the precipitated crystals.

US 2009/0088574 discloses a crystalline form of perampanel designated Form IV, which is prepared by slurring perampanel in an acetone/water mixture.

U.S. Pat. No. 7,803,818 discloses an amorphous form of perampanel which is prepared by spray drying perampanel from an acetone solution.

U.S. Pat. No. 7,718,807 discloses acid addition salts of perampanel or a hydrate thereof, wherein the acid is selected from the group consisting of benzenesulfonic acid, p-toluenesulfonic acid, hydrochloric acid, hydrobromic acid, sulfuric acid, methanesulfonic acid, fumaric acid, tartaric acid, succinic acid and benzoic acid.

There still remains an unmet need for solid state forms of perampanel having good physicochemical properties, desirable bioavailability, and advantageous pharmaceutical parameters.

SUMMARY OF THE INVENTION

The present invention provides new crystalline of perampanel, pharmaceutical compositions comprising these forms, methods for their preparation and uses thereof for treating epilepsy and seizures.

The present invention is based in part on the unexpected finding that the new forms disclosed herein possess advantageous physicochemical properties which render their processing as medicaments beneficial. The new forms of the present invention have good bioavailability as well as adequate stability characteristics enabling their incorporation into a variety of different formulations particularly suitable for pharmaceutical utility.

According to one aspect, the present invention provides an anhydrous crystalline form of perampanel (Form III) having an X-ray powder diffraction pattern with diffraction peaks at 2-theta values at about 8.7±0.1, 11.7±0.1, 12.5±0.1, and 20.0±0.1.

In one embodiment, the present invention provides an anhydrous crystalline form of perampanel (Form III) having an X-ray powder diffraction pattern with diffraction peaks at 2-theta values at about 8.7±0.1, 11.7±0.1, 12.5±0.1, 20.0±0.1, 23.3±0.1, 26.4±0.1 and 28.7±0.1.

In another embodiment, the present invention provides an anhydrous crystalline form of perampanel (Form III) having an X-ray powder diffraction pattern with diffraction peaks at 2-theta values at about 4.7±0.1, 7.8±0.1, 8.7±0.1, 9.5±0.1, 10.3±0.1, 11.7±0.1, 12.5±0.1, 14.2±0.1, 15.1±0.1, 16.1±0.1, 17.6±0.1, 19.1±0.1, 20.0±0.1, 20.5±0.1, 21.1±0.1, 21.4±0.1, 22.4±0.1, 23.3±0.1, 24.2±0.1, 25.3±0.1, 26.4±0.1, 27.2±0.1 and 28.7±0.1.

In some embodiments, the crystalline form of perampanel (Form III) is characterized by an X-ray diffraction (XRD) profile substantially as shown in FIG. 1 or in Table 1. Each possibility represents a separate embodiment of the present invention.

In other embodiments, the crystalline form of perampanel (Form III) is characterized by a DSC profile substantially as shown in FIG. 2. In another embodiment, the crystalline form of perampanel (Form III) is characterized by a TGA profile substantially as shown in FIG. 3. In some embodiments, the crystalline perampanel (Form III) of the present invention is further characterized by an IR spectrum substantially as shown in FIG. 4. In certain embodiments, the IR spectrum of the crystalline form of perampanel (Form III) comprises characteristic peaks at about 692±4, 733±4, 741±4, 783±4, 874±4, 938±4, 1033±4, 1067±4, 1132±4, 1147±4, 1185±4, 1219±4, 1246±4, 1261±4, 1276±4, 1314±4, 1368±4, 1432±4, 1455±4, 1470±4, 1550±4, 1569±4, 1588±4, 1622±4, 1656±4, 2214±4, 2351±4, 3012±4, 3050±4, 3118±4, and 3384±4 cm$^{-1}$. In certain embodiments, the crystalline perampanel (Form III) of the present invention is further characterized by a Raman spectrum substantially as shown in FIG. 5. In particular embodiments, the Raman spectrum of the crystalline perampanel (Form III) of the present invention comprises characteristic peaks at about 117±4, 141±4, 179±4, 224±4, 255±4, 265±4, 303±4, 390±4, 448±4, 479±4, 545±4, 611±4, 663±4, 745±4, 783±4, 821±4, 866±4, 980±4, 1008±4, 1036±4, 1091±4, 1129±4, 1156±4, 1181±4, 1212±4, 1236±4, 1257±4, 1277±4, 1315±4, 1360±4, 1391±4, 1426±4, 1471±4, 1540±4, 1557±4, 1585±4, 1612±4, 1657±4, 2210±4, and 3066±4 cm$^{-1}$. Each possibility represents a separate embodiment of the present invention.

In one embodiment, the present invention provides a process for preparing crystalline perampanel (Form III), the process comprising the steps of:
(a) suspending perampanel in a solvent mixture comprising MEK:water, preferably at a ratio of about 1:1 (v/v) with stirring; and
(b) isolating perampanel Form III.

In another embodiment, the present invention provides a process for preparing crystalline perampanel (Form III), the process comprising the steps of:
(a) dissolving perampanel in a solvent mixture comprising DCM:MTBE, preferably at a ratio of about 1:1 (v/v); and
(b) evaporating the solvent so as to provide perampanel Form III.

In one embodiment, the evaporation in step (b) is performed at about room temperature, preferably at about 25° C.

According to another aspect, the present invention provides an anhydrous crystalline form of perampanel (Form V) having an X-ray powder diffraction pattern with diffraction peaks at 2-theta values at about 8.8±0.1 and 11.9±0.1.

In one embodiment, the present invention provides an anhydrous crystalline form of perampanel (Form V) having an X-ray powder diffraction pattern with diffraction peaks at 2-theta values at about 8.8±0.1, 11.9±0.1 and 15.8±0.1.

In another embodiment, the present invention provides an anhydrous crystalline form of perampanel (Form V) having an X-ray powder diffraction pattern with diffraction peaks at 2-theta values at about 8.8±0.1, 11.9±0.1 and 15.8±0.1, and having no substantial peaks at 2-theta values at about 7.8±0.1, 9.5±0.1, 10.3±0.1, 14.3±0.1, 19.1±0.1 and 22.4±0.1 (i.e., peaks that are characteristic of the perampanel Form I according to the prior art).

In another embodiment, the present invention provides an anhydrous crystalline form of perampanel (Form V) having an X-ray powder diffraction pattern with diffraction peaks at 2-theta values at about 4.5±0.1, 8.8±0.1, 11.9±0.1, 14.9±0.1, 15.8±0.1, 17.9±0.1, 20.2±0.1, 21.1±0.1, 23.4±0.1, 24.6±0.1, 26.0±0.1, 27.5±0.1 and 34.0±0.1.

In some embodiments, the crystalline form of perampanel (Form V) is characterized by an X-ray diffraction (XRD) profile substantially as shown in FIG. 6 or in Table 2. Each possibility represents a separate embodiment of the present invention.

In other embodiments, the crystalline form of perampanel (Form V) is characterized by a DSC profile substantially as shown in FIG. 7. In another embodiment, the crystalline form of perampanel (Form V) is characterized by a TGA profile substantially as shown in FIG. 8. In some embodiments, the crystalline perampanel (Form V) of the present invention is further characterized by an IR spectrum substantially as shown in FIG. 9. In certain embodiments, the IR spectrum of the crystalline form of perampanel (Form V) comprises characteristic peaks at about 690±4, 727±4, 743±4, 784±4, 870±4, 943±4, 984±4, 1029±4, 1091±4, 1127±4, 1148±4, 1221±4, 1250±4, 1262±4, 1274±4, 1315±4, 1366±4, 1426±4, 1483±4, 1548±4, 1560±4, 1589±4, 1618±4, 1650±4, 2214±4, 3007±4 and 3056±4 cm$^{-1}$. In certain embodiments, the crystalline perampanel (Form V) of the present invention is further characterized by a Raman spectrum substantially as shown in FIG. 10. In particular embodiments, the Raman spectrum of the crystalline perampanel (Form V) of the present invention comprises characteristic peaks at about 120±4, 151±4, 231±4, 262±4, 290±4, 324±4, 397±4, 459±4, 538±4, 555±4, 621±4, 669±4, 749±4, 801±4, 825±4, 873±4, 908±4, 987±4, 1018±4, 1042±4, 1070±4, 1094±4, 1136±4, 1191±4, 1222±4, 1246±4, 1260±4, 1284±4, 1326±4, 1367±4, 1398±4, 1433±4, 1474±4, 1550±4, 1567±4, 1595±4, 1623±4, 1661±4, 1757±4, 1858±4, 2217±4 and 3066±4 cm$^{-1}$. Each possibility represents a separate embodiment of the present invention.

In one embodiment, the present invention provides a process for preparing crystalline perampanel (Form V), the process comprising the steps of:
(a) dissolving perampanel in a solvent or solvent mixture selected from the group consisting of DCM, MEK:1,4-dioxane, DCM:EtOH, THF:1,4-dioxane, Acetone:THF and Acetone: 1,4-dioxane; and
(b) evaporating the solvent so as to provide perampanel Form V.

In one embodiment, the evaporation in step (b) is performed at about room temperature, preferably at about 25° C. In another embodiment, the process uses a solvent mixture wherein the mixture is used at a ratio of about 1:1 (v/v).

According to another aspect, the present invention provides an anhydrous crystalline form of perampanel (Form VII) having an X-ray powder diffraction pattern with diffraction peaks at 2-theta values at about 11.6±0.1, 17.8±0.1, 24.4±0.1 and 27.6±0.1.

In one embodiment, the present invention provides an anhydrous crystalline form of perampanel (Form VII) having an X-ray powder diffraction pattern with diffraction peaks at 2-theta values at about 11.6±0.1, 17.8±0.1, 24.4±0.1 and 27.6±0.1, and having no substantial peaks at 2-theta values at about 19.1±0.1, and 22.4±0.1. (i.e., peaks that are characteristic of the perampanel Form I according to the prior art).

In another embodiment, the present invention provides an anhydrous crystalline form of perampanel (Form VII) having an X-ray powder diffraction pattern with diffraction peaks at 2-theta values at about 4.5±0.1, 7.7±0.1, 8.7±0.1, 9.4±0.1, 11.6±0.1, 12.4±0.1, 15.0±0.1, 16.0±0.1, 17.5±0.1, 17.8±0.1, 19.9±0.1, 20.9±0.1, 21.4±0.1, 23.3±0.1, 24.1±0.1, 24.4±0.1, 25.5±0.1, 27.2±0.1, 27.6±0.1 and 28.7±0.1.

In some embodiments, the crystalline form of perampanel (Form VII) is characterized by an X-ray diffraction (XRD) profile substantially as shown in FIG. 11 or in Table 3. Each possibility represents a separate embodiment of the present invention.

In other embodiments, the crystalline form of perampanel (Form VII) is characterized by a DSC profile substantially as shown in FIG. 12. In another embodiment, the crystalline form of perampanel (Form VII) is characterized by a TGA profile substantially as shown in FIG. 13. In some embodiments, the crystalline perampanel (Form VII) of the present invention is further characterized by an IR spectrum substantially as shown in FIG. 14. In certain embodiments, the IR spectrum of the crystalline form of perampanel (Form VII) comprises characteristic peaks at about 682±4, 727±4, 747±4, 780±4, 870±4, 931±4, 1025±4, 1095±4, 1131±4, 1152±4, 1213±4, 1234±4, 1262±4, 1274±4, 1311±4, 1377±4, 1434±4, 1467±4, 1548±4, 1569±4, 1585±4, 1630±4, 1657±4, 2227±4, 3007±4 and 3044±4 cm$^{-1}$. In certain embodiments, the crystalline perampanel (Form VII) of the present invention is further characterized by a Raman spectrum substantially as shown in FIG. 15. In particular embodiments, the Raman spectrum of the crystalline perampanel (Form VII) of the present invention comprises characteristic peaks at about 120±4, 151±4, 238±4, 279±4, 321±4, 400±4, 459±4, 500±4, 669±4, 749±4, 794±4, 870±4, 987±4, 1018±4, 1042±4, 1094±4, 1136±4, 1177±4, 1219±4, 1246±4, 1263±4, 1284±4, 1326±4, 1367±4, 1398±4, 1433±4, 1474±4, 1550±4, 1569±4, 1592±4, 1619±4, 2217±4 and 3070±4 cm$^{-1}$. Each possibility represents a separate embodiment of the present invention.

In one embodiment, the present invention provides a process for preparing crystalline perampanel (Form VII), the process comprising the steps of:
(a) dissolving perampanel in a solvent mixture selected from the group consisting of MEK:2-MeTHF and DCM: EtOAc; and
(b) evaporating the solvent so as to provide perampanel Form VII.

In one embodiment, the evaporation in step (b) is performed at about room temperature, preferably at about 25° C. In another embodiment, the solvent mixture is used at a ratio of about 1:1 (v/v).

The present invention also encompasses pharmaceutically acceptable salts of the new polymorphic forms of the present invention (Forms III, V and VII), including without limitation acid addition salts of perampanel, wherein the acid is, e.g., benzenesulfonic acid, p-toluenesulfonic acid, hydrochloric acid, hydrobromic acid, sulfuric acid, methanesulfonic acid, fumaric acid, tartaric acid, succinic acid or benzoic acid. Each possibility represents a separate embodiment of the present invention.

In certain embodiments, the present invention provides a pharmaceutical composition comprising the crystalline perampanel (Form III) of the present invention as an active ingredient, and a pharmaceutically acceptable carrier. In other embodiments, the present invention provides a pharmaceutical composition comprising the crystalline perampanel (Form V) of the present invention as an active ingredient, and a pharmaceutically acceptable carrier. In other embodiments, the present invention provides a pharmaceutical composition comprising the crystalline perampanel (Form VII) of the present invention as an active ingredient, and a pharmaceutically acceptable carrier.

In a particular embodiment, the pharmaceutical composition is in the form of a tablet, a capsule, a pill, a powder or a solution. In another particular embodiment, the pharmaceutical composition is in the form of a sublingual tablet, an orally disintegrating tablet or an orally disintegrating wafer. Each possibility represents a separate embodiment of the present invention.

In some embodiments, the crystalline perampanel polymorphic forms (Form III, V or VII) of the present invention are useful for treating epilepsy. In other embodiments, the crystalline perampanel polymorphic forms (Form III, V or VII) of the present invention are useful for treating seizures, e.g., partial-onset seizures with or without secondarily generalized seizures. Each possibility represents a separate embodiment of the present invention.

In various embodiments, the present invention provides a pharmaceutical composition comprising any of the crystalline perampanel polymorphic forms (Form III, V or VII) of the present invention as an active ingredient, and a pharmaceutically acceptable carrier for use in treating or preventing epilepsy or seizures.

In some embodiments, the present invention provides a method of treating or preventing epilepsy or seizures, comprising administering to a subject in need thereof an effective amount of any of the crystalline perampanel polymorphic forms (Form III, V or VII) of the present invention, or a pharmaceutical composition comprising any of these polymorphic forms.

In additional embodiments, the present invention provides the use of an effective amount of any of the crystalline perampanel polymorphic forms (Form III, V or VII) of the present invention, or a pharmaceutical composition comprising any of these polymorphic forms, for treating epilepsy or seizures.

In other embodiments, the subject is a mammal, such as a human.

Further embodiments and the full scope of applicability of the present invention will become apparent from the detailed description given hereinafter. However, it should be understood that the detailed description and examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
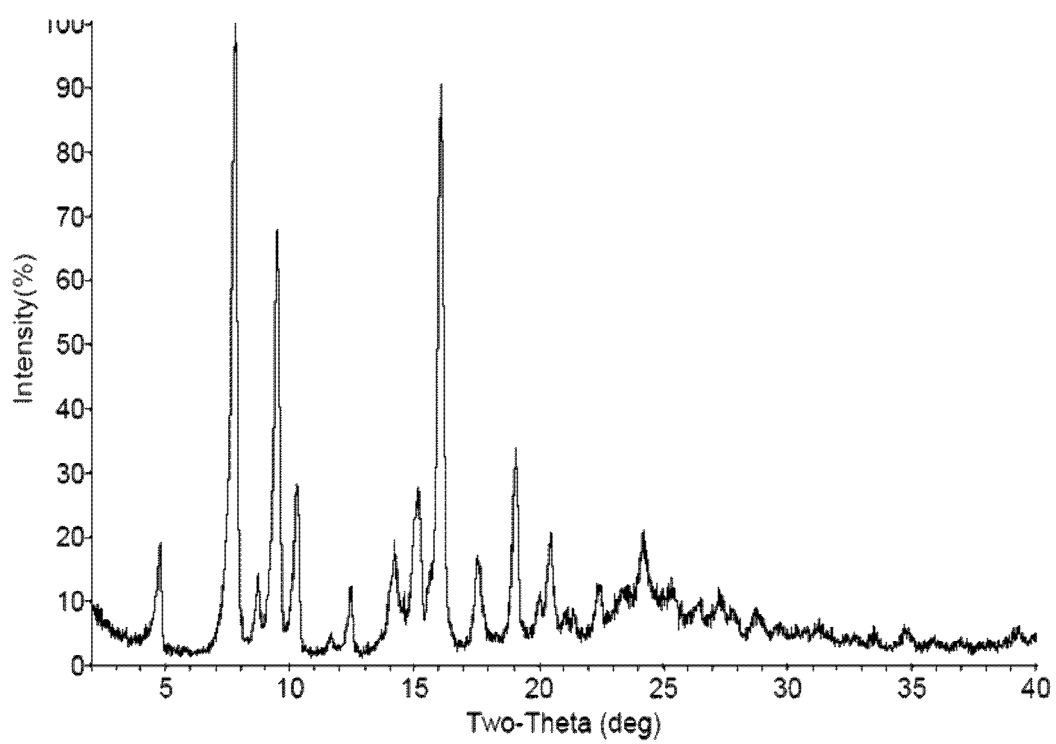
FIG. 1 illustrates a characteristic X-ray diffraction pattern of perampanel Form III according to the present invention.

The present invention is directed to three novel anhydrous crystalline forms of 3-(2-cyanophenyl)-5-(2-pyridyl)-1-phenyl-1,2-dihydropyridin-2-one (Perampanel), designated herein "Form III", "Form V" and "Form VII". These novel polymorphic forms are different from the amorphous and crystalline (anhydrous or hydrated) perampanel forms described in the prior art.

The present invention is further directed to pharmaceutical compositions comprising the crystalline perampanel forms of the present invention and a pharmaceutically acceptable carrier and their use in treating conditions and disorders for which perampanel is approved, for example epilepsy and seizures, especially partial-onset seizures with or without secondarily generalized seizures.

The present invention is further directed to methods of preparing the novel crystalline perampanel forms of the present invention.

Polymorphs are two or more solid state phases of the same chemical compound that possess different arrangement and/or conformation of the molecules. Polymorphism is the ability of a substance to exist in several different amorphous and crystalline forms. Polymorphism in pharmaceuticals is reviewed in Hancock et al. (Journal of Pharmacy and Pharmacology 2002, 54: 1151-1152), the content of which is hereby incorporated by reference. The identification and characterization of various morphic or amorphic forms of a pharmaceutically active compound is of great significance in obtaining medicaments with desired properties including a specific dissolution rate, milling property, bulk density, thermal stability or shelf-life. The novel forms of perampanel disclosed herein possess improved physicochemical properties including lower hygroscopicity, improved chemical stability at high humidity conditions (75% RH), and improved aqueous solubility.

Perampanel Crystalline Form III

Provided herein is an anhydrous crystalline perampanel (Form III) which is characterized by a unique X-ray diffraction pattern. Characteristic X-ray diffraction patterns can be seen in FIG. 1 and in Table 1 below. The X-ray diffraction pattern comprises characteristic peaks expressed in degrees 2-theta at about 8.7±0.1, 11.7±0.1, 12.5±0.1, and 20.0±0.1. In some embodiments, the X-ray diffraction pattern has additional characteristic peaks expressed in degrees 2-theta at about 23.3±0.1, 26.4±0.1 and 28.7±0.1. In further embodiments, the X-ray diffraction pattern of crystalline perampanel (Form III) has characteristic peaks expressed in degrees 2-theta at about 4.7±0.1, 7.8±0.1, 8.7±0.1, 9.5±0.1, 10.3±0.1, 11.7±0.1, 12.5±0.1, 14.2±0.1, 15.1±0.1, 16.1±0.1, 17.6±0.1, 19.1±0.1, 20.0±0.1, 20.5±0.1, 21.1±0.1, 21.4±0.1, 22.4±0.1, 23.3±0.1, 24.2±0.1, 25.3±0.1, 26.4±0.1, 27.2±0.1 and 28.7±0.1.

The crystalline perampanel (Form III) of the present invention can be further characterized by its melting point and by using various techniques including, but not limited to, infrared absorption, Raman spectrometry, and thermal analysis (e.g. thermogravimetric analysis (TGA) and differential scanning calorimetry (DSC)).

Figure 2:
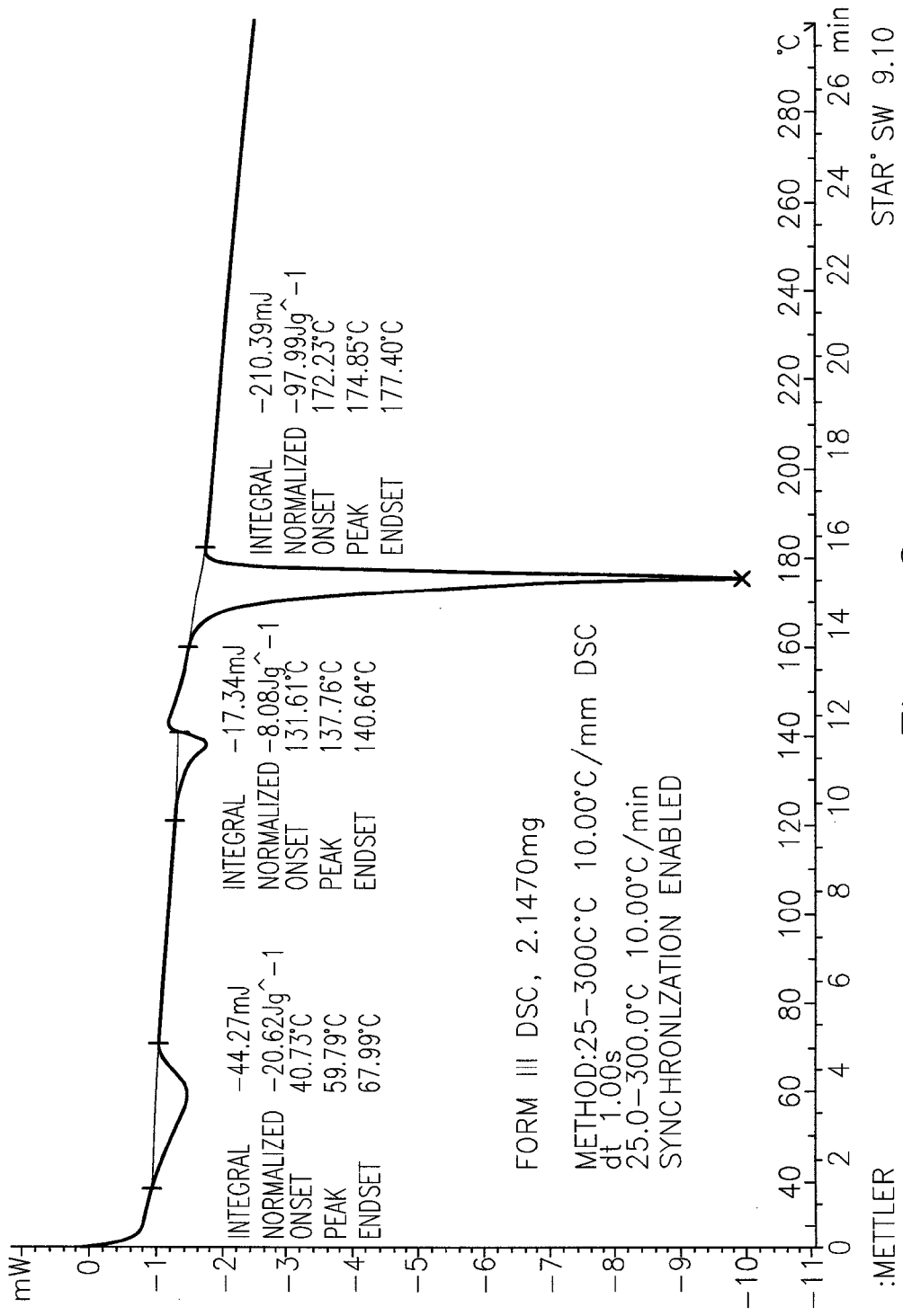
FIG. 2 illustrates a characteristic Differential Scanning calorimetry (DSC) profile of perampanel Form III according to the present invention.
Figure 3:
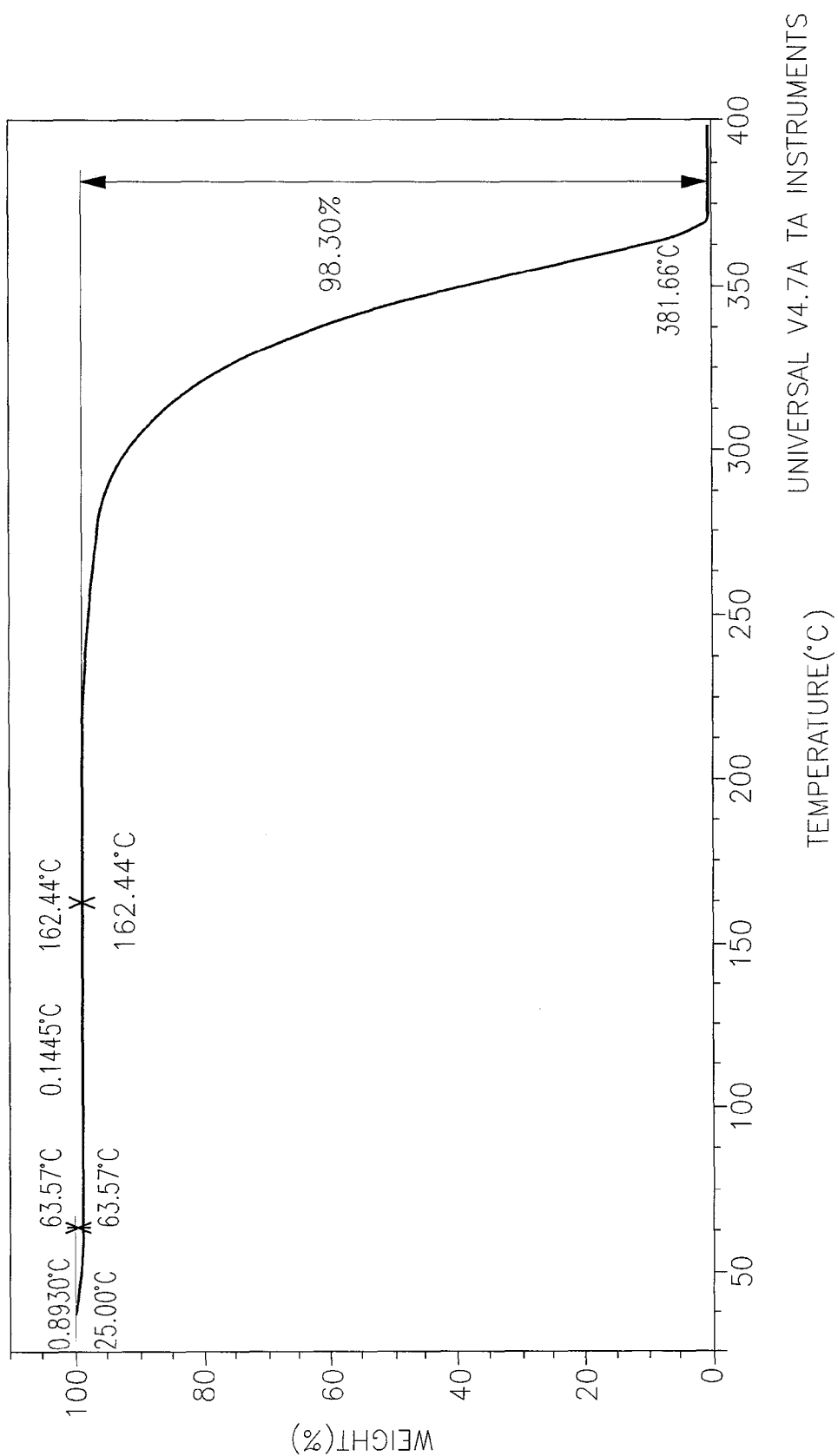
FIG. 3 illustrates a characteristic Thermogravimetric analysis (TGA) profile of perampanel Form III according to the present invention.

In certain embodiments, the crystalline perampanel (Form III) of the present invention is characterized by a DSC profile substantially as shown in FIG. 2 with a major peak at about 180° C. (onset at about 132° C. and endset at about 141° C.), and with minor peaks (shoulders) at about 60° C. (onset at about 41° C. and endset at about 68° C.), and at about 175° C. (onset at about 172° C. and endset at about 177° C.). The crystalline perampanel (Form III) may be further characterized by a TGA profile substantially as shown in FIG. 3.

Figure 4:
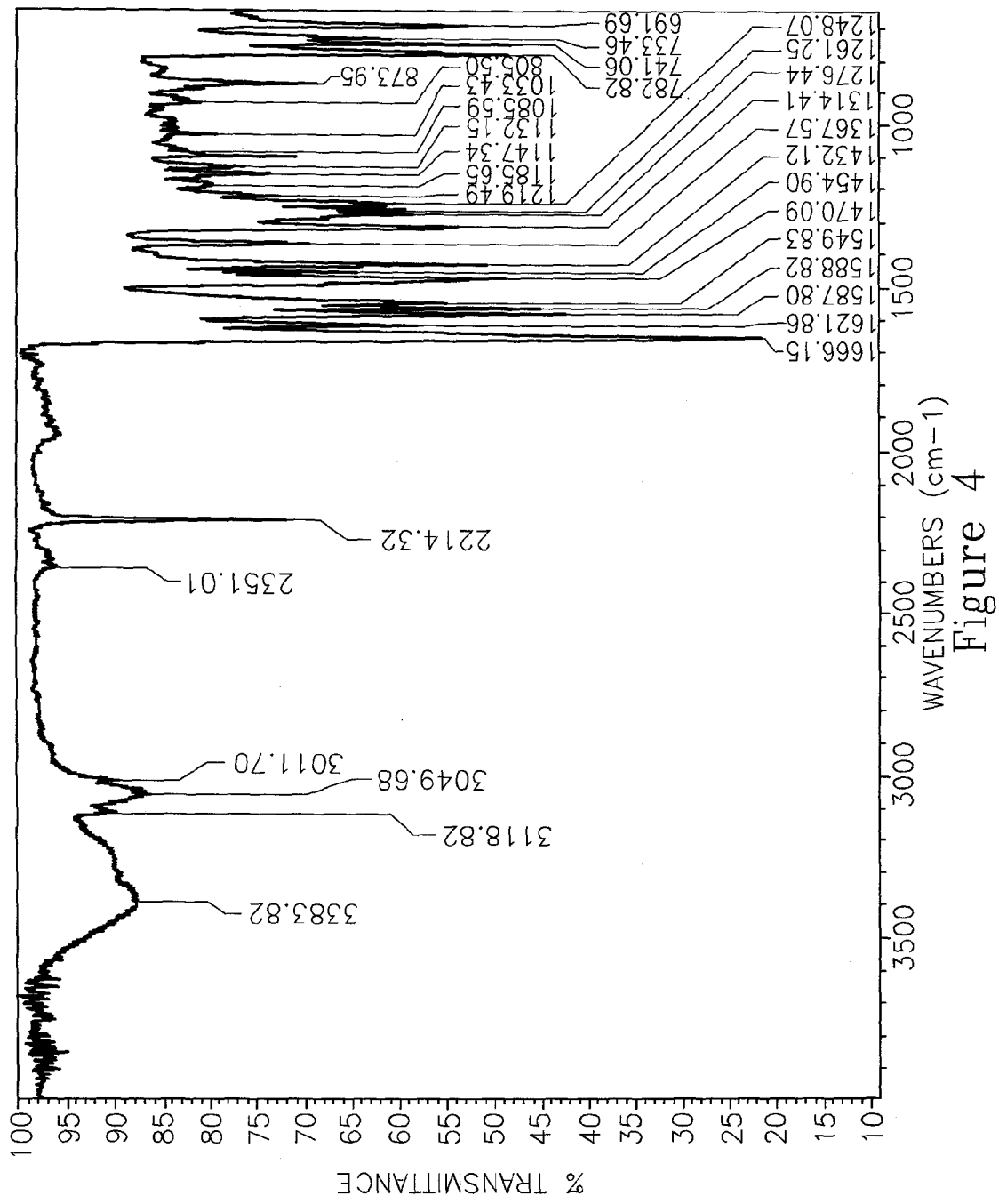
FIG. 4 illustrates a characteristic Fourier Transform Infrared (FTIR) spectrum of perampanel Form III according to the present invention.
Figure 5:
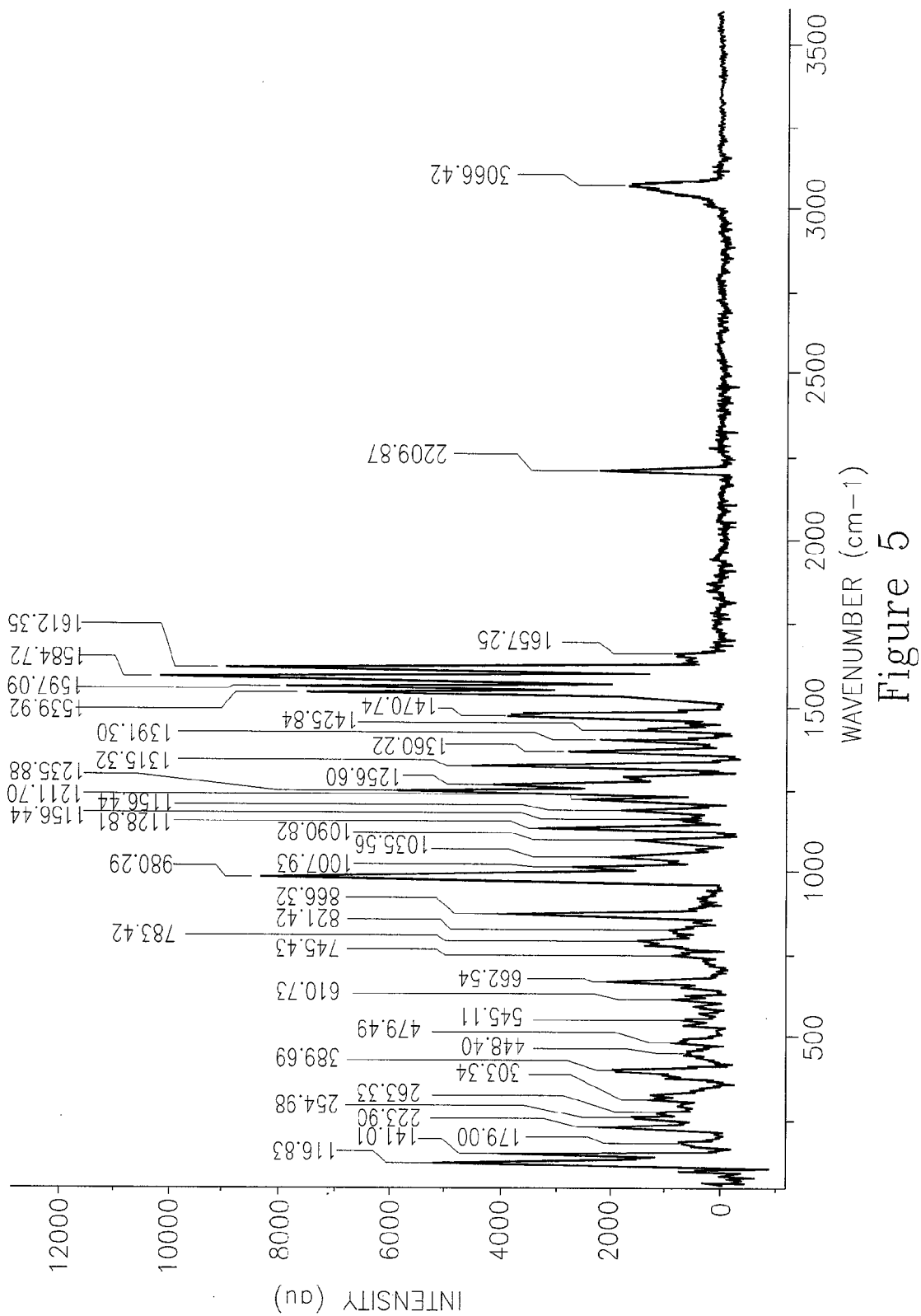
FIG. 5 illustrates a characteristic Fourier Transform-Raman (FT-Raman) spectrum of perampanel Form III according to the present invention.

In other embodiments, the crystalline perampanel (Form III) is characterized by an infrared spectrum substantially as shown in FIG. 4 with characteristic peaks at the following wavenumbers: about 692, about 733, about 741, about 783, about 874, about 938, about 1033, about 1067, about 1132, about 1147, about 1185, about 1219, about 1246, about 1261, about 1276, about 1314, about 1368, about 1432, about 1455, about 1470, about 1550, about 1569, about 1588, about 1622, about 1656, about 2214, about 2351, about 3012, about 3050, about 3118, and about 3384 cm$^{-1}$. In other embodiments, the crystalline perampanel (Form III) is characterized by a Raman spectrum substantially as shown in FIG. 5 with characteristic peaks at the following wavenumbers: about 117, about 141, about 179, about 224, about 255, about 265, about 303, about 390, about 448, about 479, about 545, about 611, about 663, about 745, about 783, about 821, about 866, 980, about 1008, about 1036, about 1091, about 1129, about 1156, about 1181, about 1212, about 1236, about 1257, about 1277, about 1315, about 1360, about 1391, about 1426, about 1471, about 1540, about 1557, about 1585, about 1612, about 1657, about 2210, and about 3066 cm$^{-1}$. Each possibility represents a separate embodiment of the present invention.

The present invention further provides processes for the preparation of crystalline perampanel (Form III). The processes include slurring in a solvent or mixtures of solvents, and/or crystallizations from saturated solutions. In one embodiment, these processes involve the use of perampanel, such as crystalline perampanel Form I (designated herein "API") as the starting material or any other perampanel known in the art, for example the perampanel described in WO 01/96308, EP 1764361 (US 2010/324297), US 2009/0088574, U.S. Pat. No. 7,803,818 and U.S. Pat. No. 7,718,807, the contents of each of which are hereby incorporated by reference in their entirety. Alternatively, the perampanel starting material can be made in accordance with any method known in the art, including, for example, the methods described in WO 01/96308, EP 1764361 (US 2010/324297), US 2009/0088574, U.S. Pat. No. 7,803,818 and U.S. Pat. No. 7,718,807. In one embodiment, the perampanel starting material is suspended in a suitable solvent or solvent mixture, e.g., methyl ethyl ketone (MEK):water, preferably at a ratio of about 1:1 (v/v) with stirring or shaking, and the resulting product (perampanel Form III) is isolated from the suspension. In another embodiment, the perampanel starting material is dissolved in a suitable solvent e.g., dichloromethane (DCM):methyl t-butyl ether (MTBE), preferably at a ratio of about 1:1 (v/v), at room temperatures or at temperatures below the boiling point of the solvent. The solvent is then slowly evaporated at room temperature (about 20° C. to about 30° C., for example at about 25° C.). Optionally, the solutions are filtered before solvent evaporation begins.

Perampanel Crystalline Form V

Provided herein is an anhydrous crystalline perampanel (Form V) which is characterized by a unique X-ray diffraction pattern. Characteristic X-ray diffraction patterns can be seen in FIG. 6 and in Table 2 below. The X-ray diffraction pattern comprises characteristic peaks expressed in degrees 2-theta at about 8.8±0.1 and 11.9±0.1. In some embodiments, the X-ray diffraction pattern has an additional characteristic peak expressed in degrees 2-theta at about 15.8±0.1. In further embodiments, the X-ray diffraction pattern of crystalline perampanel (Form V) has characteristic peaks expressed in degrees 2-theta at about 8.8±0.1, 11.9±0.1 and 15.8±0.1, and having no substantial peaks at 2-theta values at about 7.8±0.1, 9.5±0.1, 10.3±0.1, 14.3±0.1, 19.1±0.1 and 22.4±0.1 (i.e., peaks that are characteristic of the perampanel Form I according to the prior art). In further embodiments, the X-ray diffraction pattern of crystalline perampanel (Form III) has characteristic peaks expressed in degrees 2-theta at about 4.5±0.1, 8.8±0.1, 11.9±0.1, 14.9±0.1, 15.8±0.1, 17.9±0.1, 20.2±0.1, 21.1±0.1, 23.4±0.1, 24.6±0.1, 26.0±0.1, 27.5±0.1 and 34.0±0.1.

The crystalline perampanel (Form V) of the present invention can be further characterized by its melting point and by using various techniques including, but not limited to, infrared absorption, Raman spectrometry, and thermal analysis (e.g. thermogravimetric analysis (TGA) and differential scanning calorimetry (DSC)).

Figure 7:
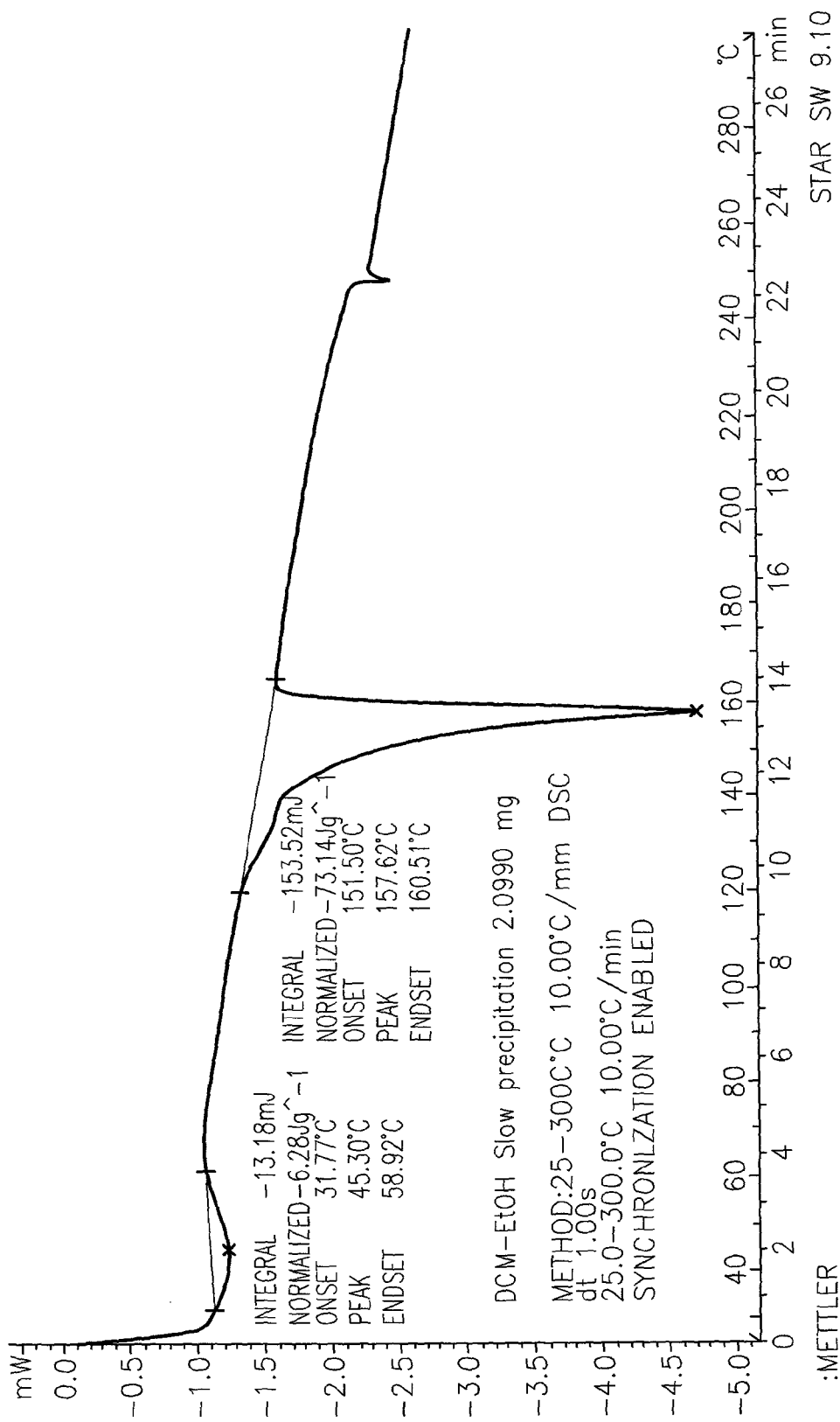
FIG. 7 illustrates a characteristic Differential Scanning calorimetry (DSC) profile of perampanel Form V according to the present invention.
Figure 8:
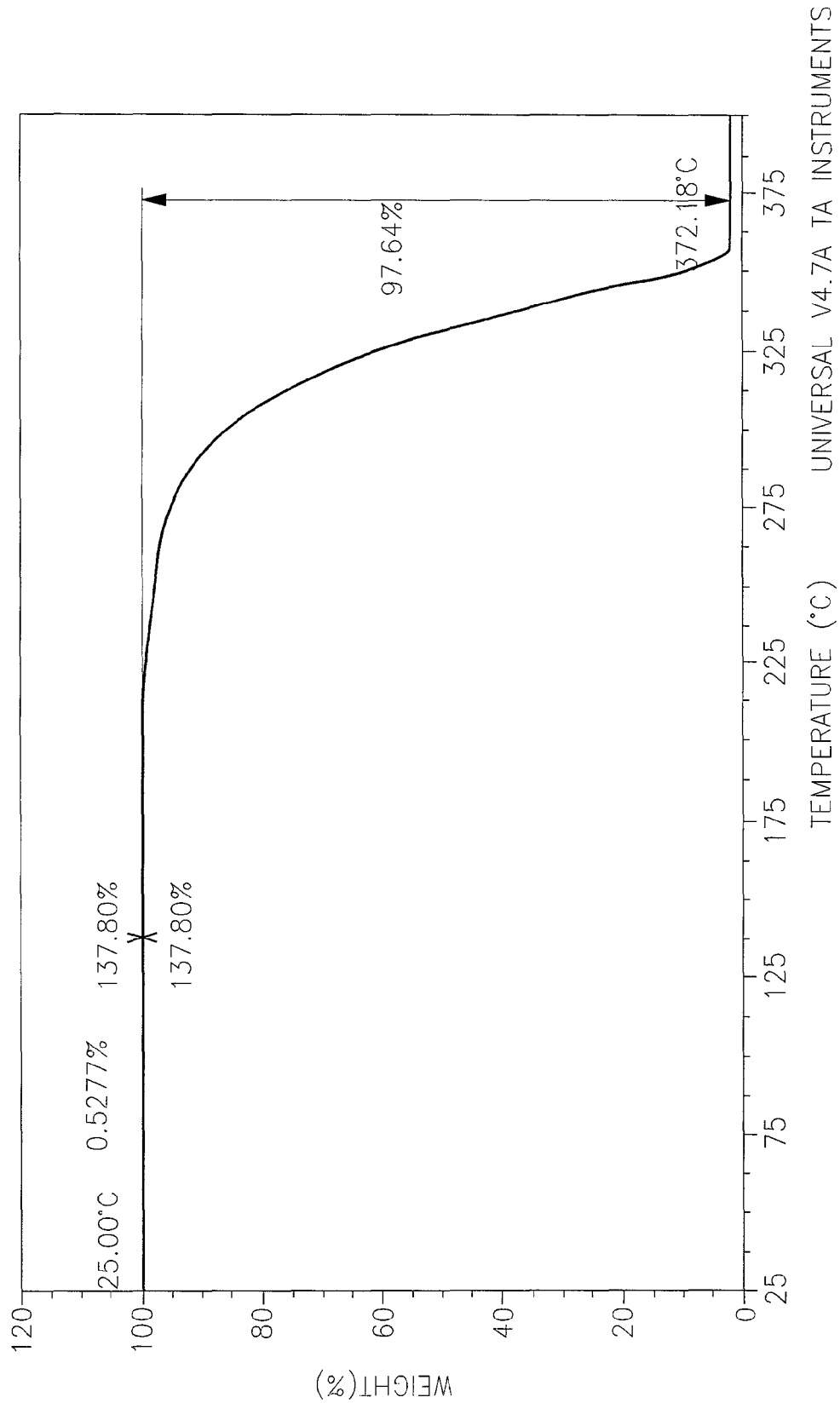
FIG. 8 illustrates a characteristic Thermogravimetric analysis (TGA) profile of perampanel Form V according to the present invention.

In certain embodiments, the crystalline perampanel (Form V) of the present invention is characterized by a DSC profile substantially as shown in FIG. 7 with a major peak at about 158° C. (onset at about 151° C. and endset at about 160° C.), and with a minor peak (shoulder) at about 45° C. (onset at about 32° C. and endset at about 59° C.). The crystalline perampanel (Form V) may be further characterized by a TGA profile substantially as shown in FIG. 8.

Figure 9:
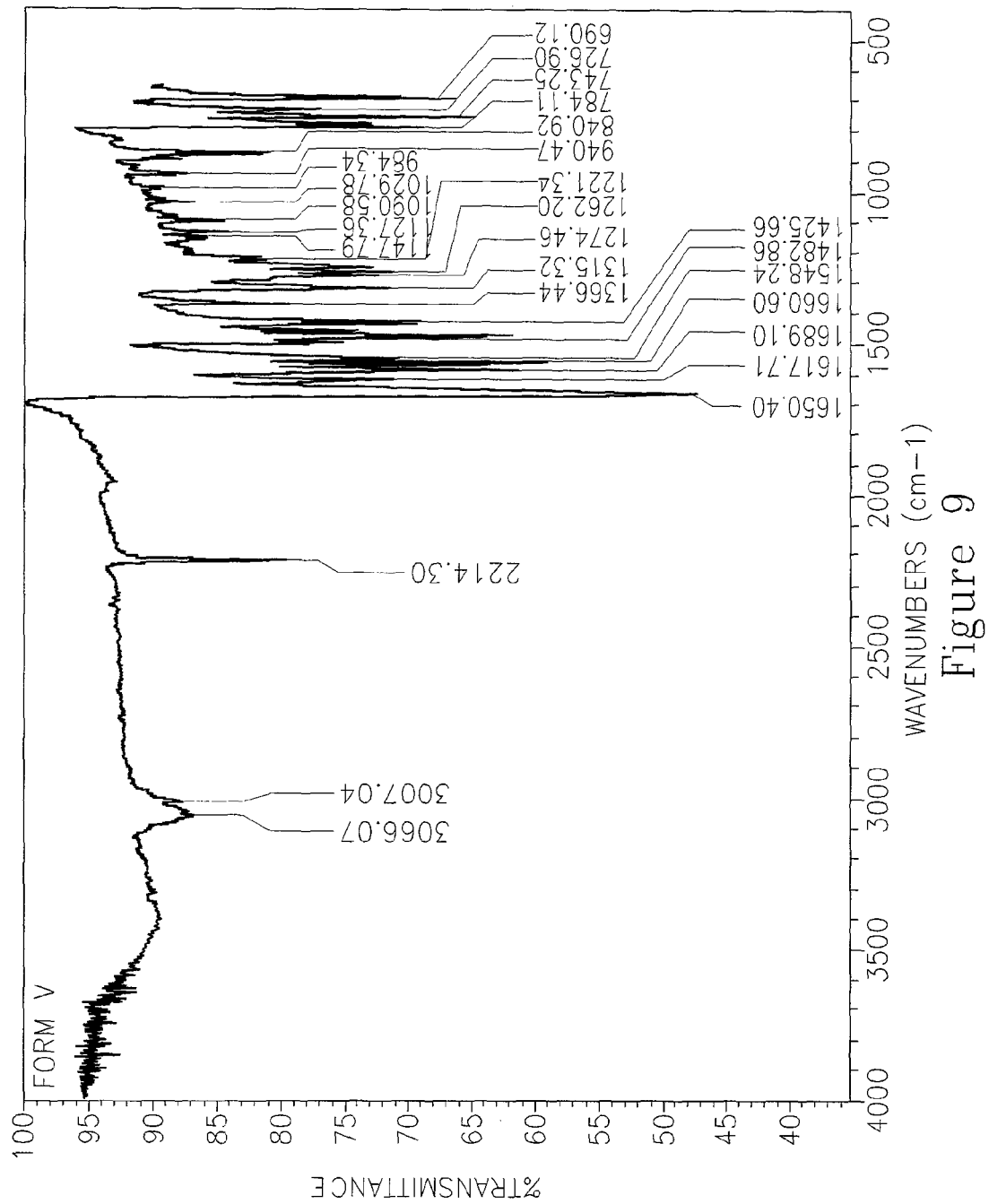
FIG. 9 illustrates a characteristic Fourier Transform Infrared (FTIR) spectrum of perampanel Form V according to the present invention.
Figure 10:
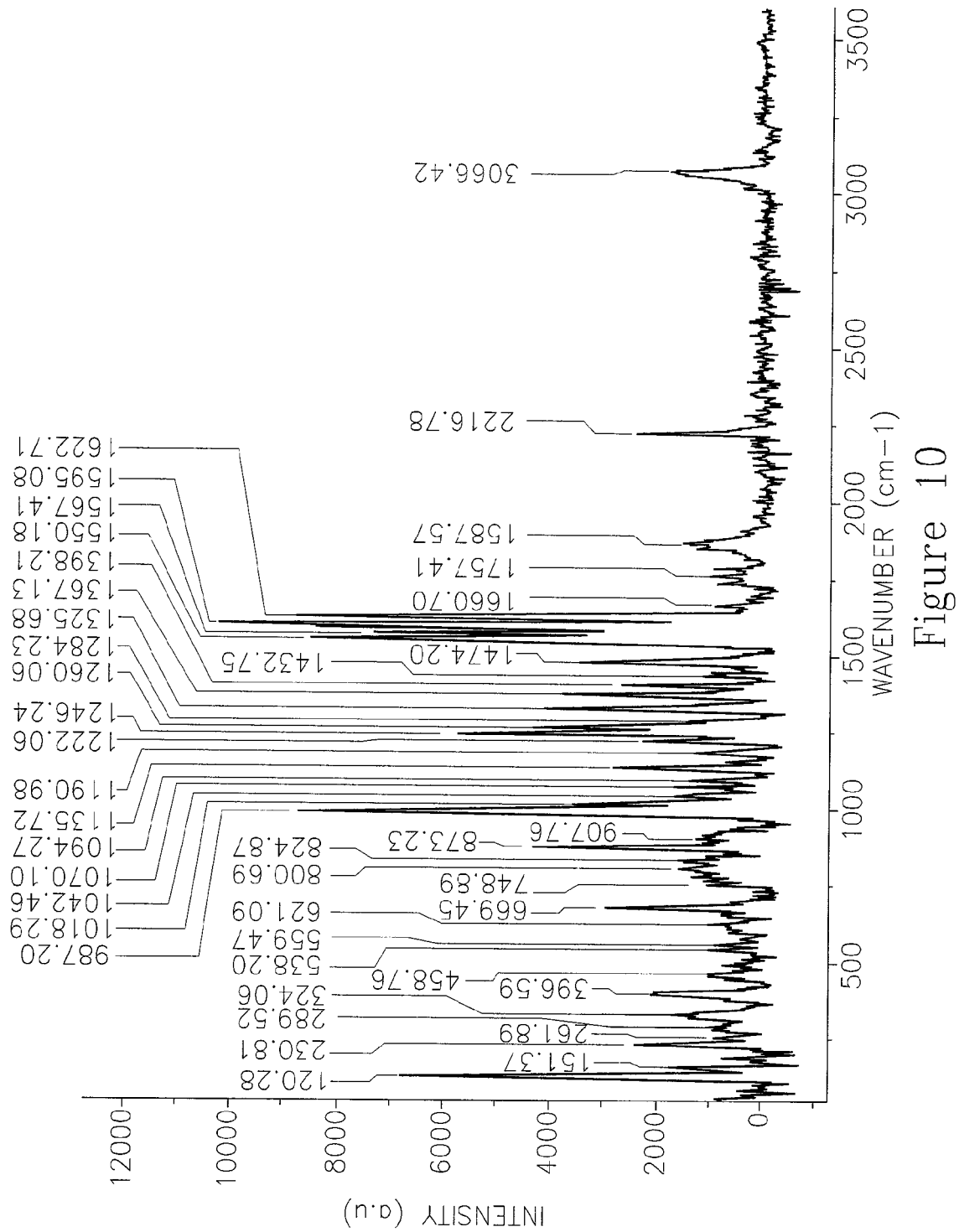
FIG. 10 illustrates a characteristic Fourier Transform-Raman (FT-Raman) spectrum of perampanel Form V according to the present invention.

In other embodiments, the crystalline perampanel (Form V) is characterized by an infrared spectrum substantially as shown in FIG. 9 with characteristic peaks at the following wavenumbers: about 690, about 727, about 743, about 784, about 870, about 943, about 984, about 1029, about 1091, about 1127, about 1148, about 1221, about 1250, about 1262, about 1274, about 1315, about 1366, about 1426, about 1483, about 1548, about 1560, about 1589, about 1618, about 1650, about 2214, about 3007 and about 3056 cm$^{-1}$. In other embodiments, the crystalline perampanel (Form V) is characterized by a Raman spectrum substantially as shown in FIG. 10 with characteristic peaks at the following wavenumbers: about 120, about 151, about 231, about 262, about 290, about 324, about 397, about 459, about 538, about 555, about 621, about 669, about 749, about 801, about 825, about 873, about 908, about 987, about 1018, about 1042, about 1070, about 1094, about 1136, about 1191, about 1222, about 1246, about 1260, about 1284, about 1326, about 1367, about 1398, about 1433, about 1474, about 1550, about 1567, about 1595, about 1623, 1661, about 1757, about 1858, about 2217 and about 3066 cm$^{-1}$. Each possibility represents a separate embodiment of the present invention.

The present invention further provides processes for the preparation of crystalline perampanel (Form V). The processes include crystallizations from saturated solutions. In one embodiment, these processes involve the use of perampanel, such as crystalline perampanel Form I (API) as the starting material or any other perampanel known in the art, for example the perampanel described in WO 01/96308, EP 1764361 (US 2010/324297), US 2009/0088574, U.S. Pat. No. 7,803,818 and U.S. Pat. No. 7,718,807, the contents of each of which are hereby incorporated by reference in their entirety. Alternatively, the perampanel starting material can be made in accordance with any method known in the art, including, for example, the methods described in WO 01/96308, EP 1764361 (US 2010/324297), US 2009/0088574, U.S. Pat. No. 7,803,818 and U.S. Pat. No. 7,718,807. In one embodiment, the perampanel starting material is dissolved in a suitable solvent or mixtures of solvents, e.g., DCM, MEK:1,4-dioxane, DCM:EtOH, tetrahydrofuran (THF):1,4-dioxane, Acetone:THF and Acetone:1,4-dioxane preferably at a ratio of about 1:1 (v/v), at room temperatures or at temperatures below the boiling point of the solvent. The solvent is then slowly evaporated at room temperature (about 20° C. to about 30° C., for example at about 25° C.). Optionally, the solutions are filtered before solvent evaporation begins.

Perampanel Crystalline Form VII

Provided herein is an anhydrous crystalline perampanel (Form VII) which is characterized by a unique X-ray diffraction pattern. Characteristic X-ray diffraction patterns can be seen in FIG. 7 and in Table 3 below. The X-ray diffraction pattern comprises characteristic peaks expressed in degrees 2-theta at about 11.6±0.1, 17.8±0.1, 24.4±0.1 and 27.6±0.1. In further embodiments, the X-ray diffraction pattern of crystalline perampanel (Form VII) has characteristic peaks expressed in degrees 2-theta at about 11.6±0.1, 17.8±0.1, 24.4±0.1 and 27.6±0.1, and having no substantial peaks at 2-theta values at about 19.1±0.1, and 22.4±0.1. (i.e., peaks that are characteristic of the perampanel Form I according to the prior art). In further embodiments, the X-ray diffraction pattern of crystalline perampanel (Form III) has characteristic peaks expressed in degrees 2-theta at about 4.5±0.1, 7.7±0.1, 8.7±0.1, 9.4±0.1, 11.6±0.1, 12.4±0.1, 15.0±0.1, 16.0±0.1, 17.5±0.1, 17.8±0.1, 19.9±0.1, 20.9±0.1, 21.4±0.1, 23.3±0.1, 24.1±0.1, 24.4±0.1, 25.5±0.1, 27.2±0.1, 27.6±0.1 and 28.7±0.1, as set forth in Table 3 below.

The crystalline perampanel (Form VII) of the present invention can be further characterized by its melting point and by using various techniques including, but not limited to, infrared absorption, Raman spectrometry, and thermal analysis (e.g. thermogravimetric analysis (TGA) and differential scanning calorimetry (DSC)).

Figure 12:
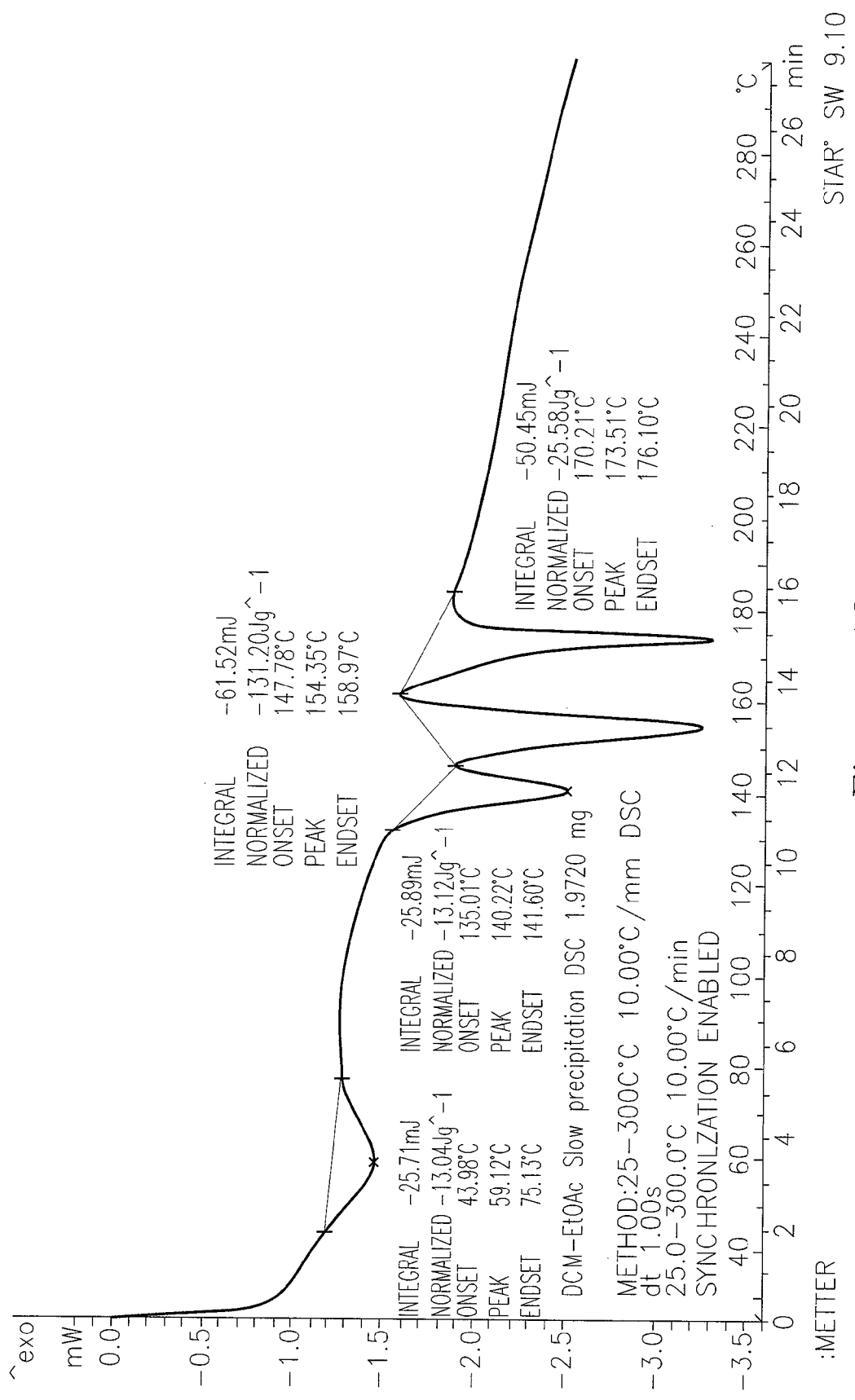
FIG. 12 illustrates a characteristic Differential Scanning calorimetry (DSC) profile of perampanel Form VII according to the present invention.
Figure 13:
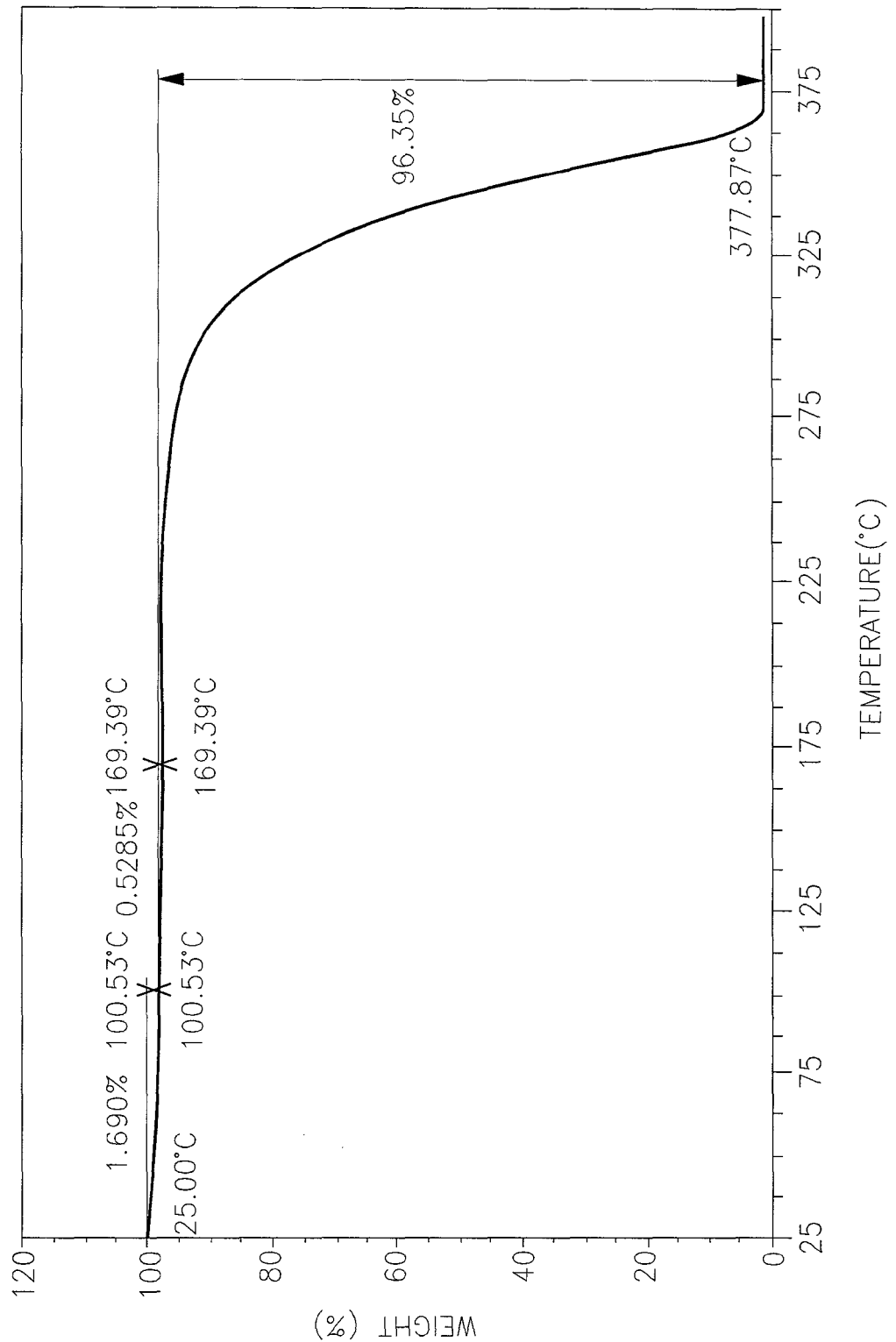
FIG. 13 illustrates a characteristic Thermogravimetric analysis (TGA) profile of perampanel Form VII according to the present invention.

In certain embodiments, the crystalline perampanel (Form VII) of the present invention is characterized by a DSC profile substantially as shown in FIG. 12 with peaks at about 140° C. (onset at about 135° C. and endset at about 145° C.), 154° C. (onset at about 148° C. and endset at about 159° C.), 173° C. (onset at about 170° C. and endset at about 176° C.), and with a minor peak (shoulder) at about 59° C. (onset at about 44° C. and endset at about 75° C.). The crystalline perampanel (Form VII) may be further characterized by a TGA profile substantially as shown in FIG. 13.

Figure 14:
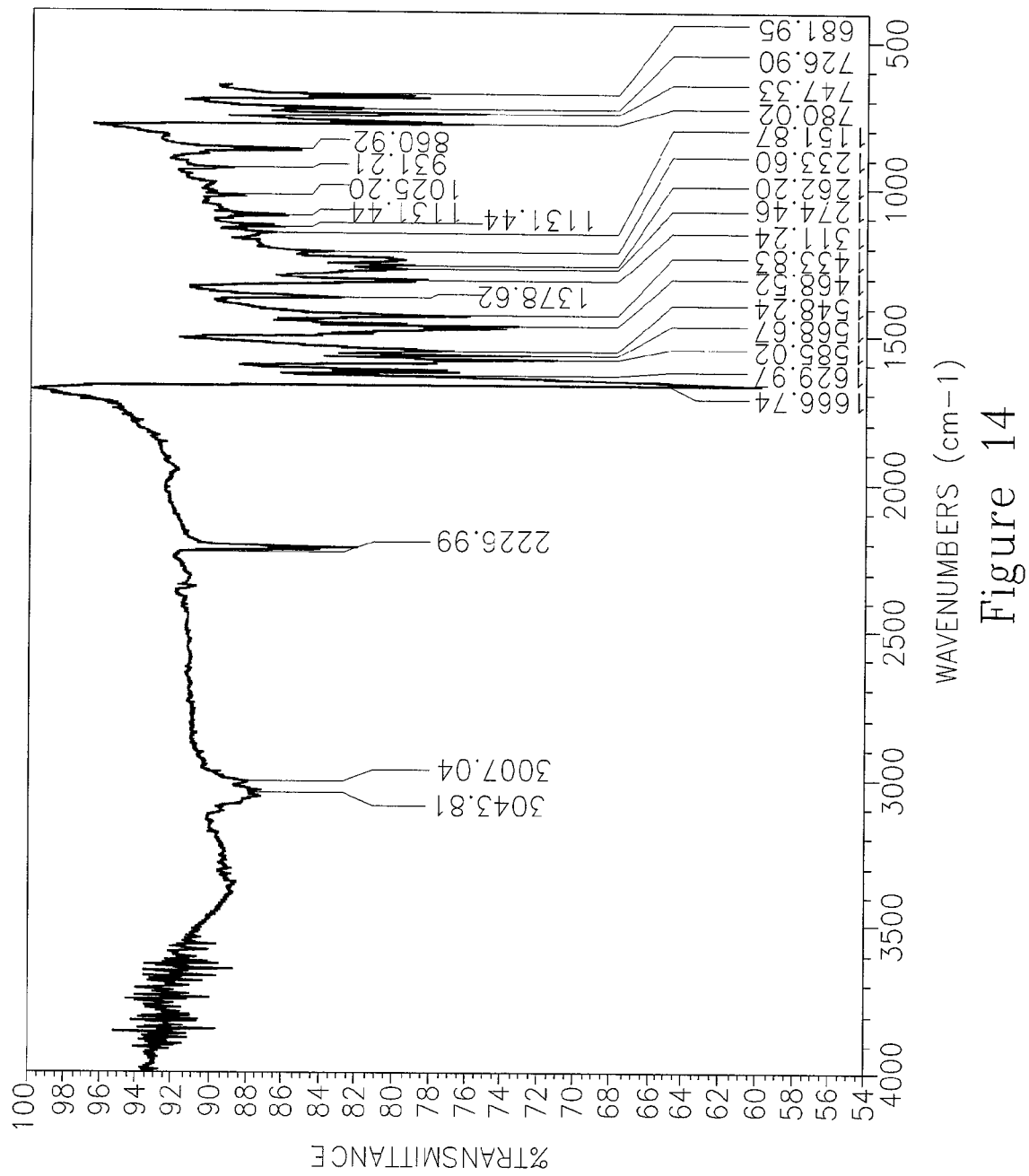
FIG. 14 illustrates a characteristic Fourier Transform Infrared (FTIR) spectrum of perampanel Form VII according to the present invention.
Figure 15:
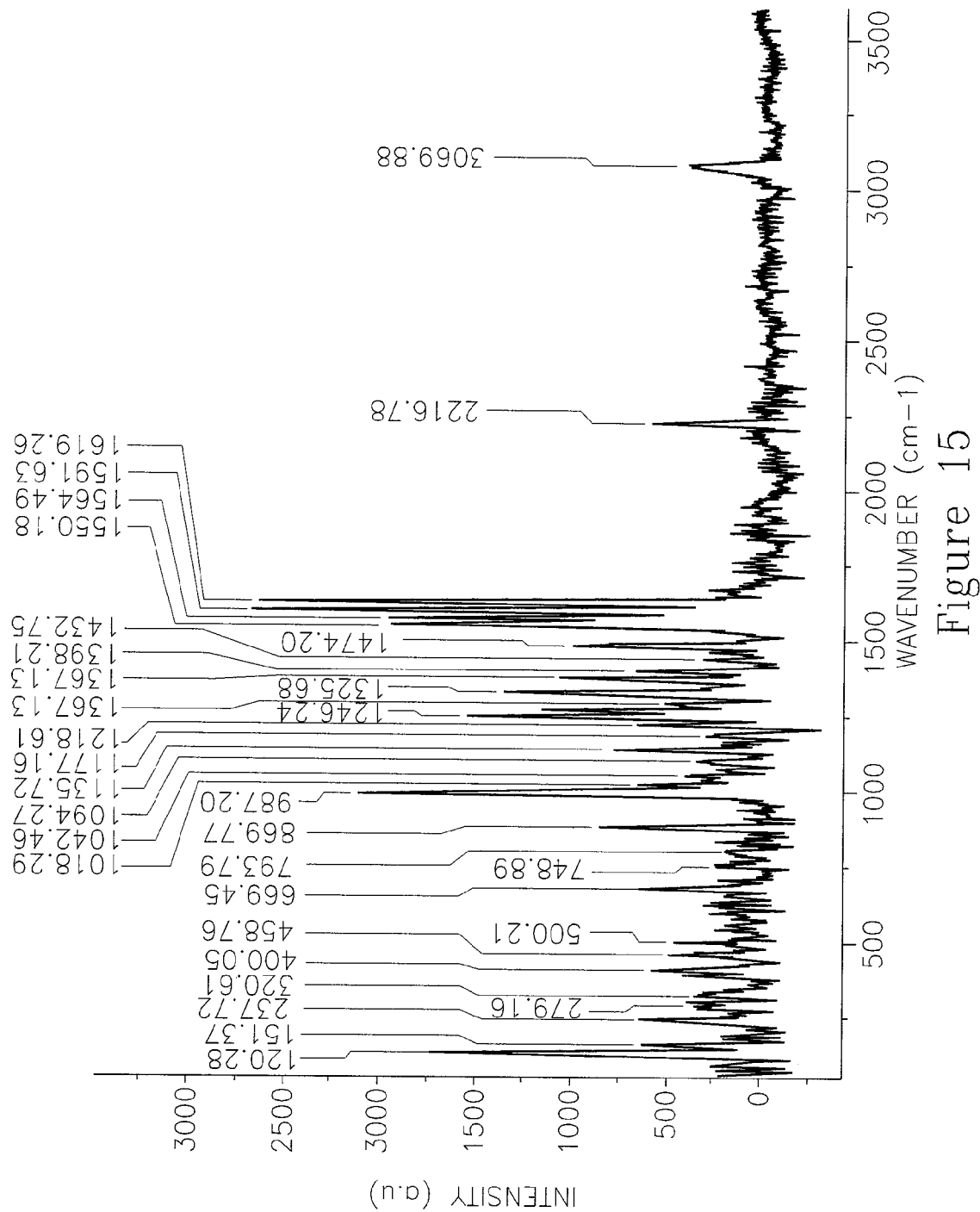
FIG. 15 illustrates a characteristic Fourier Transform-Raman (FT-Raman) spectrum of perampanel Form VII according to the present invention.

In other embodiments, the crystalline perampanel (Form VII) is characterized by an infrared spectrum substantially as shown in FIG. 14 with characteristic peaks at the following wavenumbers: about 682, about 727, about 747, about 780, about 870, about 931, about 1025, about 1095, about 1131, about 1152, about 1213, about 1234, about 1262, about 1274, about 1311, about 1377, about 1434, about 1467, about 1548, about 1569, about 1585, about 1630, about 1657, about 2227, about 3007 and about 3044 $cm^{-1}$. In other embodiments, the crystalline perampanel (Form VII) is characterized by a Raman spectrum substantially as shown in FIG. 15 with characteristic peaks at the following wavenumbers: about 120, about 151, about 238, about 279, about 321, about 400, about 459, about 500, about 669, about 749, about 794, about 870, about 987, about 1018, about 1042, about 1094, about 1136, about 1177, about 1219, about 1246, about 1263, about 1284, about 1326, about 1367, about 1398, about 1433, about 1474, about 1550, about 1569, about 1592, about 1619, about 2217 and about 3070 $cm^{-1}$. Each possibility represents a separate embodiment of the present invention.

The present invention further provides processes for the preparation of crystalline perampanel (Form VII). The processes include crystallizations from saturated solutions. In one embodiment, these processes involve the use of perampanel, such as crystalline perampanel Form I (API) as the starting material or any other perampanel known in the art, for example the perampanel described in WO 01/96308, EP 1764361 (US 2010/324297), US 2009/0088574, U.S. Pat. No. 7,803,818 and U.S. Pat. No. 7,718,807, the contents of each of which are hereby incorporated by reference in their entirety. Alternatively, the perampanel starting material can be made in accordance with any method known in the art, including, for example, the methods described in WO 01/96308, EP 1764361 (US 2010/324297), US 2009/0088574, U.S. Pat. No. 7,803,818 and U.S. Pat. No. 7,718,807. In one embodiment, the perampanel starting material is dissolved in a suitable solvent or mixtures of solvents, e.g., MEK:2-MeTHF and DCM:EtOAc preferably at a ratio of about 1:1 (v/v), at room temperatures or at temperatures below the boiling point of the solvent. The solvent is then slowly evaporated at room temperature (about 20° C. to about 30° C., for example at about 25° C.). Optionally, the solutions are filtered before solvent evaporation begins.

Pharmaceutical Compositions and Therapeutic Methods

The novel forms of the present invention are useful for the treatment of epilepsy and related conditions and disorders such as seizures and/or convulsions. The present invention thus provides pharmaceutical compositions comprising the novel perampanel crystalline forms disclosed herein and a pharmaceutically acceptable carrier. The pharmaceuticals can be safely administered orally or non-orally. Routes of administration include, but are not limited to, oral, topical, mucosal, nasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural and sublingual. Typically, the perampanel forms of the present invention are administered orally. The pharmaceutical compositions can be formulated as tablets (including e.g. film-coated tablets), powders, granules, capsules (including soft capsules), orally disintegrating tablets, and sustained-release preparations as is well known in the art.

Pharmacologically acceptable carriers that may be used in the context of the present invention include various organic or inorganic carriers including, but not limited to, excipients, lubricants, binders, disintegrants, water-soluble polymers and basic inorganic salts. The pharmaceutical compositions of the present invention may further include additives such as, but not limited to, preservatives, antioxidants, coloring agents, sweetening agents, souring agents, bubbling agents and flavorings.

Suitable excipients include e.g. lactose, D-mannitol, starch, cornstarch, crystalline cellulose, light silicic anhydride and titanium oxide. Suitable lubricants include e.g. magnesium stearate, sucrose fatty acid esters, polyethylene glycol, talc and stearic acid. Suitable binders include e.g. hydroxypropyl cellulose, hydroxypropylmethyl cellulose, crystalline cellulose, a-starch, polyvinylpyrrolidone, gum arabic powder, gelatin, pullulan and low-substitutional hydroxypropyl cellulose. Suitable disintegrants include e.g. crosslinked povidone (any crosslinked 1-ethenyl-2-pyrrolidinone homopolymer including polyvinylpyrrolidone (PVPP) and 1-vinyl-2-pyrrolidinone homopolymer), crosslinked carmellose sodium, carmellose calcium, carboxymethyl starch sodium, low-substituted hydroxypropyl cellulose, cornstarch and the like. Suitable water-soluble polymers include e.g. cellulose derivatives such as hydroxypropyl cellulose, polyvinylpyrrolidone, hydroxypropylmethyl cellulose, methyl cellulose and carboxymethyl cellulose sodium, sodium polyacrylate, polyvinyl alcohol, sodium alginate, guar gum and the like.

Suitable preservatives include e.g. sodium benzoate, benzoic acid, and sorbic acid. Suitable antioxidants include e.g. sulfites, ascorbic acid and α-tocopherol. Suitable coloring agents include e.g. food colors such as Food Color Yellow No. 5, Food Color Red No. 2 and Food Color Blue No. 2 and the like. Suitable sweetening agents include e.g. dipotassium glycyrrhetinate, aspartame, stevia and thaumatin. Suitable souring agents include e.g. citric acid (citric anhydride), tartaric acid and malic acid. Suitable bubbling agents include e.g. sodium bicarbonate. Suitable flavorings include synthetic substances or naturally occurring substances, including e.g. lemon, lime, orange, menthol and strawberry.

The perampanel forms of the present invention are particularly suitable for oral administration in the form of tablets including sublingual tablet, capsules, pills, dragées, powders, granules, solutions, orally disintegrating wafers, orally disintegrating tablets, and the like. A tablet may be made by compression or molding, optionally with one or more excipients as is known in the art. For example, molded tablets may be made by molding in a suitable machine a mixture of the powdered active ingredient moistened with an inert liquid diluent.

The tablets and other solid dosage forms of the pharmaceutical compositions described herein may optionally be scored or prepared with coatings and shells, such as enteric coatings and other coatings well known in the art. They may also be formulated so as to provide slow or controlled release of the active ingredient therein using, for example, hydroxypropylmethyl cellulose in varying proportions to provide the desired release profile, other polymer matrices and the like. The active ingredient can also be in micro-encapsulated form, if appropriate, with one or more of the above-described excipients.

The present invention provides a method of treating epilepsy or seizures comprising administering to a subject in need thereof a therapeutically effective amount of a composition comprising any one of the perampanel forms disclosed herein, for example the crystalline perampanel (Form III), the crystalline perampanel (Form V), or the crystalline perampanel (Form VII) described herein.

"A therapeutically effective amount" as used herein refers to an amount of an agent which is effective, upon single or multiple dose administration to the subject in providing a therapeutic benefit to the subject. In one embodiment, the therapeutic benefit is prevention, cessation, halting and reducing the incidence of seizures or convulsions that are associated with epileptic attacks. the perampanel forms of the present invention are used for the preparation of an anti-epileptic medicaments.

The present invention further provides the administration of the perampanel forms of the present invention in combination therapy with one or more other active ingredients. The combination therapy may include the two or more active ingredients within a single pharmaceutical composition as well as the two or more active ingredients in two separate pharmaceutical compositions administered to the same subject simultaneously or at a time interval determined by a skilled artisan.

The principles of the present invention are demonstrated by means of the following non-limiting examples.

EXAMPLES

Example 1

General Preparation Methods of Perampanel Forms

1. Reagents
Methanol, HPLC grade, Merck, Lot No. SF1SF61610
Ethanol, HPLC grade, Sigma, Lot No. 01096JK
IPA, HPLC grade, Sigma, Lot No. 63596KK
Acetonitrile, HPLC grade, Merck, Lot No. 1F1IF61294
1-Butanol, AR, Shanghai Runjie Chemical Regent Co., Ltd, Lot No. 20110315
Acetone, AR, Shanghai Runjie Chemical Regent Co., Ltd, Lot No. 20110315
MEK (methyl ethyl ketone), AR, Sinopharm Chemical Regent Co., Ltd, Lot No. T20070315
MIBK (methyl isobutyl ketone), AR, Sinopharm Chemical Regent Co., Ltd, Lot No. T20080411
Ethyl Acetate, AR, Shanghai Shiyan Chemical Regent Co., Ltd, Lot No. 20110630
iPrOAc (isopropyl acetate), AR, Shanghai Shiyan Chemical Regent Co., Ltd, Lot No. 20110419
MTBE (methyl t-butyl ether), AR, Sinopharm Chemical Regent Co., Ltd, Lot No. 20110531
THF (tetrahydrofuran), HPLC grade, Merck, Lot No. IL8IF58153
2-MeTHF (2-methyl tetrahydrofuran), AR, Shanghai Jiachen Chemical Regent Co., Ltd, Lot No. 20000665
NMP (N-methylpyrrolidone), AR, Sinopharm Chemical Regent Co., Ltd, Lot No. T 20100825
DMSO (dimethylsulfoxide), HPLC grade, Sigma, Lot No. 27496KK
Dichloromethane, AR, Shanghai Runjie Chemical Regent Co., Ltd, Lot No. 20110315
Heptane, AR, Sinopharm Chemical Regent Co., Ltd, Lot No. T 20110324
Toluene, AR, Shanghai Runjie Chemical Regent Co., Ltd, Lot No. 20110315
DMF (dimethylformamide), AR, Shanghai Runjie Chemical Regent Co., Ltd, Lot No. 20110601
1,4-Dioxane, AR, Shanghai Runjie Chemical Regent Co., Ltd, Lot No. 20110415
Purified Water 2. Instruments
Sartorius CP 225D Balance
Mettler Toledo MX5 Balance
ELGA Water Purification Equipment
Mettler Toledo DSC 1
TA Q5000 IR TGA
Rigaku D/MAX 2200 X-ray powder diffractometer
Thermo Nicolet 380 FT-IR
NMR Varian 400
Nikon LV 100 Polarized Light Microscopy
Jobin Yvon LabRam-1B FT-Raman 3. XRPD, DSC, TGA, Polarized Light Microscope, FT-IR, FT-Raman, PSD and HPLC Methods 3.1 XRPD Method
Details of XRPD method used in the tests are mentioned below:
  X-ray Generator: Cu, kα, (λ=1.54056 Å).
  Tube Voltage: 40 kV, Tube Current: 40 mA.
  DivSlit: 1 deg.
  DivH.L.Slit: 10 mm
  SctSlit: 1 deg.
  RecSlit: 0.15 mm
  Monochromator: Fixed Monochromator
  Scanning Scope: 2-40 deg.
  Scanning Step: 10 deg/min 3.2 DSC and TGA Methods
Details of DSC method used in the tests are mentioned below:
  Heat from 25° C. to 300° C. at 10° C./min
Details of TGA method used in the tests are mentioned below:
  Heat from 25° C. to 400° C. at 10° C./min 3.3 Polarized Light Microscope Method
Details of polarized light microscope method used in the tests are mentioned below:
  Nikon LV 100 POL equipped with 5 megapixel CCD
  Ocular lens: 10×
  Objective lens: 20×

3.4 FT-IR and FT-Raman Method
Details of FT-IR method used in the tests are mentioned below:
  No. of scan: 32
  Time for collection: 38 s
  Scan Range: 600-4000 cm$^{-1}$
  Resolution: 4
Details of FT-Raman method used in the tests are mentioned below:
  Laser wave: 632.8 nm
  Power: 1 mW
  Resolution: 1 cm$^{-1}$
  Time for integration: 50 s 3.5 NMR Method Details of NMR method used in the tests are mentioned below:

| F2 - Acquisition Parameters | |
|---|---|
| INSTRUM: | spect |
| PROBHD: | 5 mm QNP 1H/13PUL |
| PROG | zg30 |
| TD | 65536 |
| SOLVENT | MeOD |
| NS | 8 |
| DS | 0 |
| SWH | 8223.685 Hz |
| FIDRES | 0.125483 Hz |
| AQ | 3.9846387 sec |
| RG | 2050 |
| DW | 60.800 usec |
| DE | 6.00 usec |
| TE | 300.0 K |
| D1 | 1.00000000 sec |
| TD0 | 1 |
| CHANNEL f1 | |
| NUC1 | 1H |
| P1 | 15.30 usec |
| PL1 | 0.00 dB |
| SFO1 | 400.1324710 MHz |
| F2 - Processing parameters | |
| SI | 32768 |
| SF | 400.1299733 MHz |
| WDW | no |
| SSB | 0 |
| LB | 0.00 Hz |
| GB | 0 |
| PC | 1.00 |

4. General Preparation Methods 4.1 Method I: Slurry Method

Suspensions of Perampanel (Form I) in different solvents or mixtures of solvents were prepared and kept shaking for 24 hrs. The residues were characterized by XRPD, DSC, TGA, FT-IR and FT-Raman. Perampanel Form III was identified by this method, as set forth in the Examples below.

4.2 Method II: Slow Precipitation from Saturated Solutions

Solutions of Perampanel Form I in various solvents and solvent mixtures were prepared and filtered through 0.22 μm filter into clean vessels. Solvents were evaporated at 25° C. Formed crystals were characterized by XRPD, DSC, TGA, FT-IR and FT-Raman.

Example 2

Perampanel Form III (Method I)

General method I was performed. Thus, a suspension of perampanel (Form I) was prepared in methyl ethyl ketone (MEK):water 1:1 (v/v) and kept shaking for 24 hours. Perampanel crystalline Form III was obtained by this method.

Example 3

Perampanel Form III (Method II)

General method II was performed. A solution of Perampanel Form I in DCM:MTBE 1:1 (v/v) was prepared and filtered through 0.22 μm filter into clean vessels. Solvents were evaporated at 25° C. Perampanel crystalline Form III was obtained by this method.

The perampanel crystalline Form III obtained by Method I or Method II was characterized by an X-ray diffraction pattern (FIG. 1). The characteristic X-ray diffraction peaks are listed in Table 1. FIG. 2 illustrates a characteristic DSC profile of perampanel Form III. The DSC profile shows a major peak at about 180° C. (onset at about 132° C. and endset at about 141° C.), and with minor peaks (shoulders) at about 60° C. (onset at about 41° C. and endset at about 68° C.), and at about 175° C. (onset at about 172° C. and endset at about 177° C.). FIG. 3 illustrates a characteristic TGA profile of perampanel Form III with about 0.89% weight loss up to about 64° C., about 0.14% weight loss from about 64° C. to about 162° C., and about 98.3% weight loss from about 200° C. to about 382° C. FIG. 4 illustrates characteristic IR spectra of crystalline perampanel Form III with characteristic peaks at the following wavenumbers: about 692, about 733, about 741, about 783, about 874, about 938, about 1033, about 1067, about 1132, about 1147, about 1185, about 1219, about 1246, about 1261, about 1276, about 1314, about 1368, about 1432, about 1455, about 1470, about 1550, about 1569, about 1588, about 1622, about 1656, about 2214, about 2351, about 3012, about 3050, about 3118, and about 3384 cm$^{-1}$. FIG. 5 illustrates a characteristic FT-Raman spectrum with characteristic peaks at the following wavenumbers: about 117, about 141, about 179, about 224, about 255, about 265, about 303, about 390, about 448, about 479, about 545, about 611, about 663, about 745, about 783, about 821, about 866, 980, about 1008, about 1036, about 1091, about 1129, about 1156, about 1181, about 1212, about 1236, about 1257, about 1277, about 1315, about 1360, about 1391, about 1426, about 1471, about 1540, about 1557, about 1585, about 1612, about 1657, about 2210, and about 3066 cm$^{-1}$.

TABLE 1

| No. | 2-Theta | Intensity (%) |
|---|---|---|
| 1 | 4.7 | 17.1 |
| 2 | 7.8 | 100.0 |
| 3 | 8.7 | 12.1 |
| 4 | 9.5 | 67.2 |
| 5 | 10.3 | 26.8 |
| 6 | 11.7 | 3.2 |
| 7 | 12.5 | 10.7 |
| 8 | 14.2 | 17.3 |
| 9 | 15.1 | 25.3 |
| 10 | 16.1 | 89.3 |
| 11 | 17.6 | 15.6 |
| 12 | 19.1 | 30.4 |
| 13 | 20.0 | 7.2 |
| 14 | 20.5 | 16.5 |
| 15 | 21.1 | 3.5 |
| 16 | 21.4 | 4.0 |
| 17 | 22.4 | 6.0 |
| 18 | 23.3 | 7.4 |
| 19 | 24.2 | 16.4 |
| 20 | 25.3 | 9.0 |
| 21 | 26.4 | 4.9 |
| 22 | 27.2 | 8.6 |
| 23 | 28.7 | 4.3 |

Example 4

Perampanel Form V (Method II)

General method II was performed. Solutions of Perampanel Form I in DCM, MEK:1,4-dioxane, DCM:EtOH, THF: 1,4-dioxane, Acetone:THF or Acetone: 1,4-dioxane, were prepared and filtered through 0.22 μm filter into clean vessels. When a solvent mixture was used, the ratio of solvents was 1:1 (v/v). Solvents were evaporated at 25° C.

Figure 6:
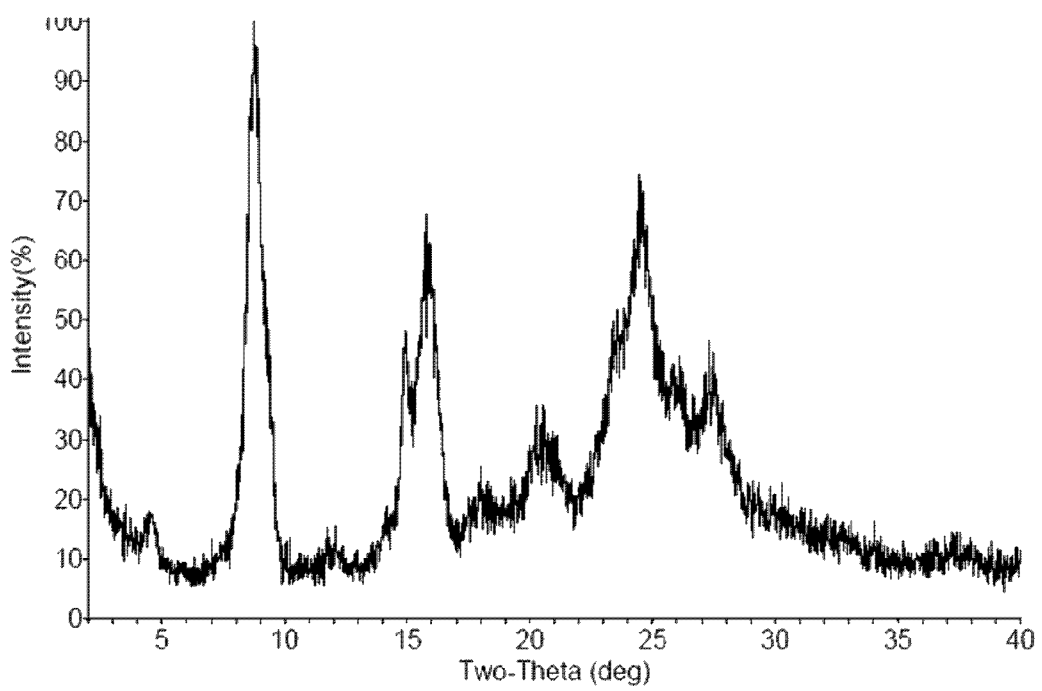
FIG. 6 illustrates a characteristic X-ray diffraction pattern of perampanel Form V according to the present invention.

Perampanel Form V obtained by this method was characterized by an X-ray diffraction pattern (FIG. 6). The characteristic X-ray diffraction peaks are listed in Table 2. FIG. 7 illustrates a characteristic DSC profile of perampanel Form V. The DSC profile shows with a major peak at about 158° C. (onset at about 151° C. and endset at about 160° C.), and with a minor peak (shoulder) at about 45° C. (onset at about 32° C. and endset at about 59° C.). FIG. 8 illustrates a characteristic TGA profile of perampanel Form V with about 0.53% weight loss up to about 138° C., and about 97.6% weight loss from about 225° C. to about 372° C. FIG. 9 illustrates characteristic IR spectra of crystalline perampanel Form V with characteristic peaks at the following wavenumbers: about 690, about 727, about 743, about 784, about 870, about 943, about 984, about 1029, about 1091, about 1127, about 1148, about 1221, about 1250, about 1262, about 1274, about 1315, about 1366, about 1426, about 1483, about 1548, about 1560, about 1589, about 1618, about 1650, about 2214, about 3007 and about 3056 cm$^{-1}$. FIG. 10 illustrates a characteristic FT-Raman spectrum with characteristic peaks at the following wavenumbers: about 120, about 151, about 231, about 262, about 290, about 324, about 397, about 459, about 538, about 555, about 621, about 669, about 749, about 801, about 825, about 873, about 908, about 987, about 1018, about 1042, about 1070, about 1094, about 1136, about 1191, about 1222, about 1246, about 1260, about 1284, about 1326, about 1367, about 1398, about 1433, about 1474, about 1550, about 1567, about 1595, about 1623, 1661, about 1757, about 1858, about 2217 and about 3066 cm$^{-1}$.

TABLE 1

Peak search report of XRPD of Form V

| No. | 2-Theta | Intensity (%) |
|---|---|---|
| 1 | 4.520 | 6.7 |
| 2 | 8.760 | 100 |
| 3 | 11.944 | 4.0 |
| 4 | 14.900 | 39.7 |
| 5 | 15.780 | 60.0 |
| 6 | 17.881 | 15.5 |
| 7 | 20.199 | 15.9 |
| 8 | 21.114 | 13.1 |
| 9 | 23.360 | 31.7 |
| 10 | 24.619 | 57.3 |
| 11 | 25.982 | 24.6 |
| 12 | 27.478 | 28.5 |
| 13 | 34.041 | 7.0 |

Example 5

Perampanel Form VII (Method II)

General method II was performed. Solutions of Perampanel Form I in MEK:2-MeTHF or DCM:EtOAc 1:1 (v/v), were prepared and filtered through 0.22 μm filter into clean vessels. Solvents were evaporated at 25° C.

Figure 11:
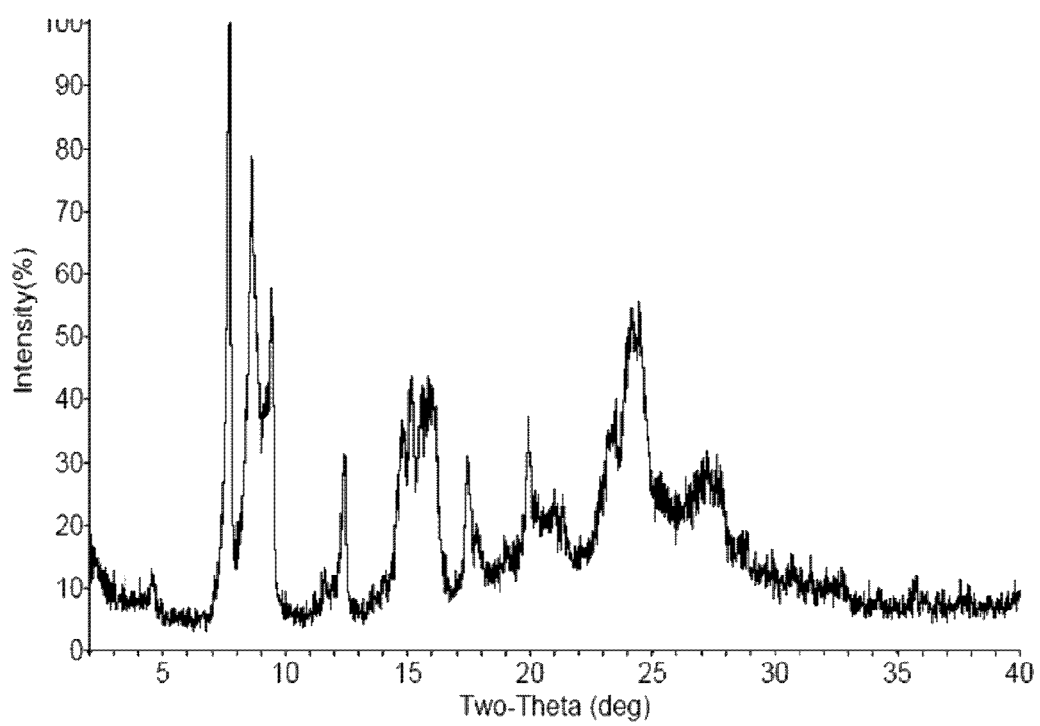
FIG. 11 illustrates a characteristic X-ray diffraction pattern of perampanel Form VII according to the present invention.

Perampanel Form VII obtained by this method was characterized by an X-ray diffraction pattern (FIG. 11). The characteristic X-ray diffraction peaks are listed in Table 3. FIG. 12 illustrates a characteristic DSC profile of perampanel Form VII. The DSC profile shows with peaks at about 140° C. (onset at about 135° C. and endset at about 145° C.), 154° C. (onset at about 148° C. and endset at about 159° C.), 173° C. (onset at about 170° C. and endset at about 176° C.), and with a minor peak (shoulder) at about 59° C. (onset at about 44° C. and endset at about 75° C.). FIG. 13 illustrates a characteristic TGA profile of perampanel Form VII with about 1.70% weight loss up to about 100° C., about 0.53% weight loss up from about 100° C. to a temperature of about 169° C., and about 96.3% weight loss from about 225° C. to about 377° C. FIG. 14 illustrates characteristic IR spectra of crystalline perampanel Form VII with characteristic peaks at the following wavenumbers: about 682, about 727, about 747, about 780, about 870, about 931, about 1025, about 1095, about 1131, about 1152, about 1213, about 1234, about 1262, about 1274, about 1311, about 1377, about 1434, about 1467, about 1548, about 1569, about 1585, about 1630, about 1657, about 2227, about 3007 and about 3044 cm$^{-1}$. FIG. 15 illustrates a characteristic FT-Raman spectrum with characteristic peaks at the following wavenumbers: about 120, about 151, about 238, about 279, about 321, about 400, about 459, about 500, about 669, about 749, about 794, about 870, about 987, about 1018, about 1042, about 1094, about 1136, about 1177, about 1219, about 1246, about 1263, about 1284, about 1326, about 1367, about 1398, about 1433, about 1474, about 1550, about 1569, about 1592, about 1619, about 2217 and about 3070 cm$^{-1}$.

TABLE 3

Peak search report of XRPD of Form VII

| No. | 2-Theta | Intensity (%) |
|---|---|---|
| 1 | 4.510 | 5.8 |
| 2 | 7.737 | 100 |
| 3 | 8.660 | 77.4 |
| 4 | 9.439 | 55.2 |
| 5 | 11.640 | 7.5 |
| 6 | 12.382 | 26.7 |
| 7 | 15.021 | 28.0 |
| 8 | 16.022 | 34.2 |
| 9 | 17.460 | 26.5 |
| 10 | 17.819 | 15.0 |
| 11 | 19.940 | 25.6 |
| 12 | 20.920 | 10.1 |
| 13 | 21.356 | 11.3 |
| 14 | 23.319 | 22.8 |
| 15 | 24.141 | 42.4 |
| 16 | 24.441 | 43.9 |
| 17 | 25.499 | 14.2 |
| 18 | 27.239 | 20.3 |
| 19 | 27.636 | 22.4 |
| 20 | 28.690 | 12.5 |

Reference Example 6

Perampanel Form I

Figure 16:
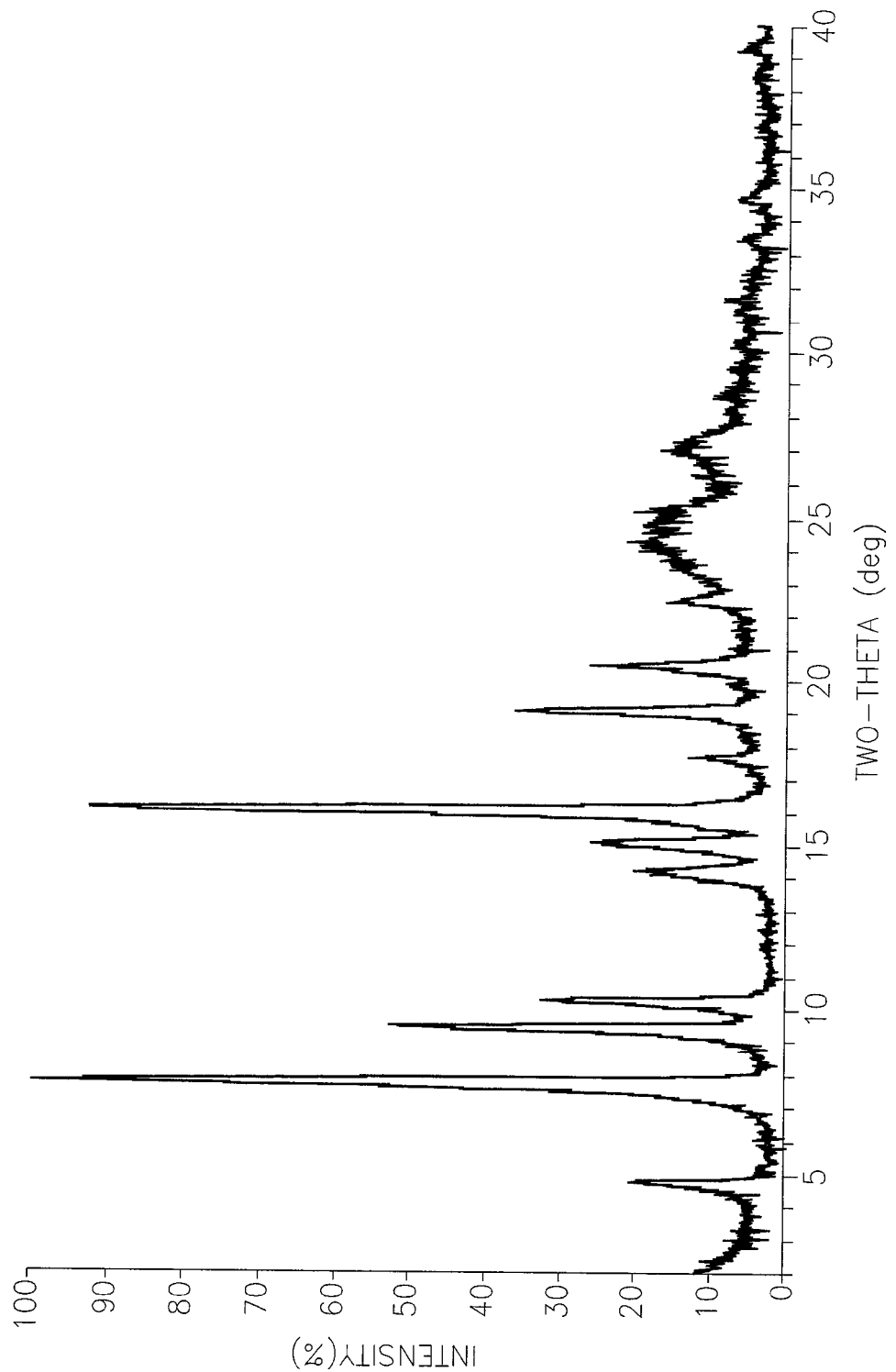
FIG. 16 illustrates a characteristic X-ray diffraction pattern of perampanel Form I.
Figure 17:
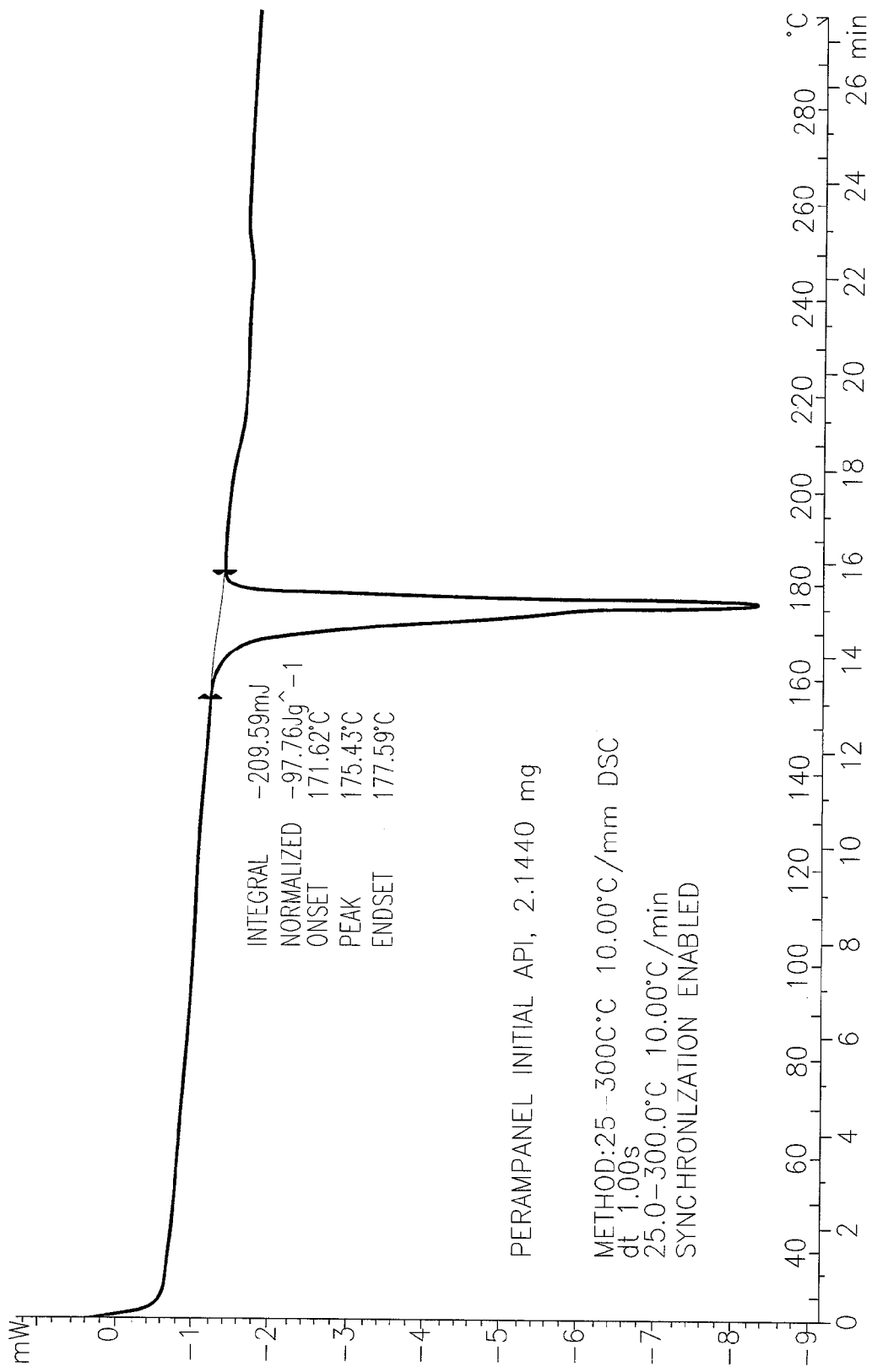
FIG. 17 illustrates a characteristic Differential Scanning calorimetry (DSC) profile of perampanel Form I.
Figure 18:
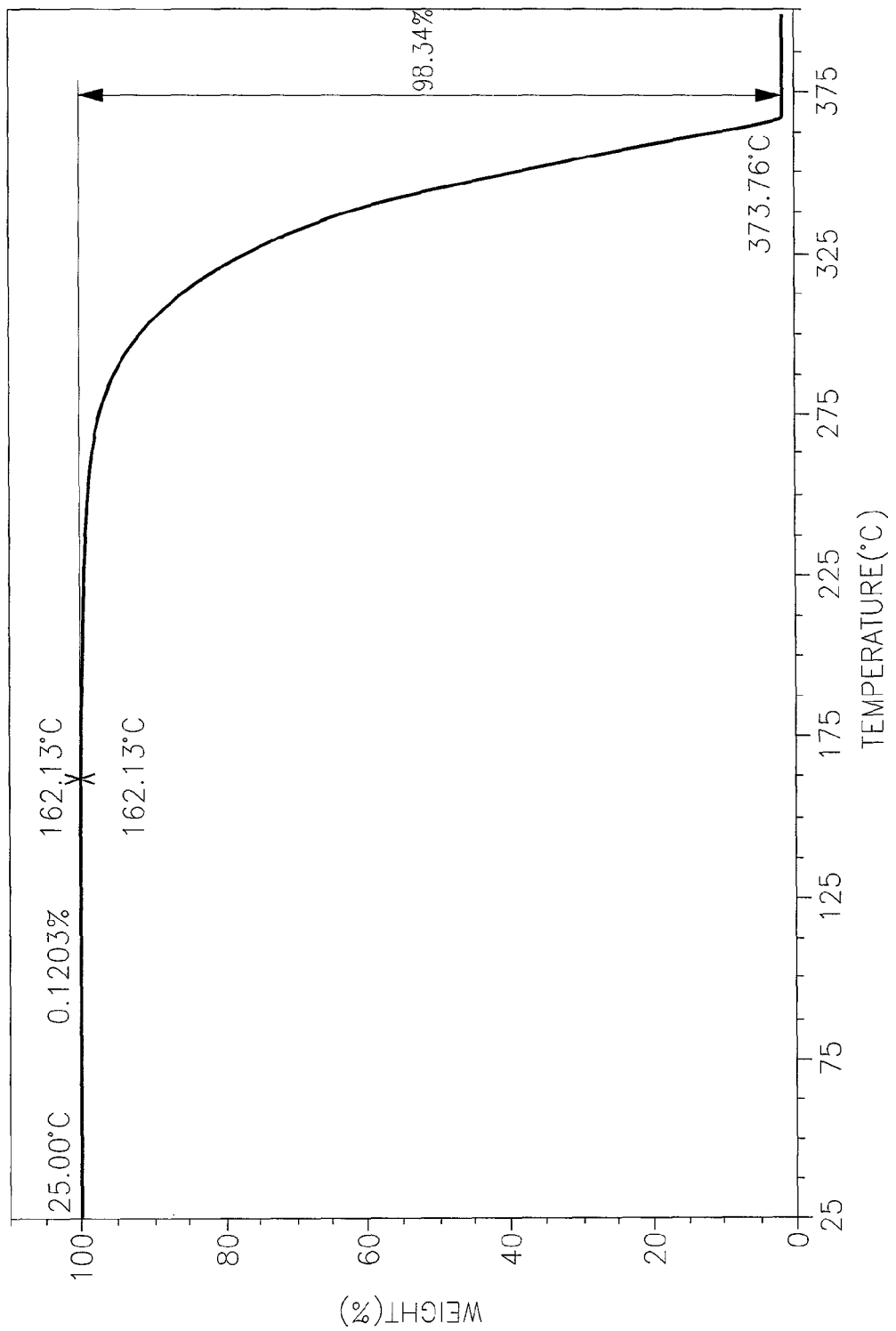
FIG. 18 illustrates a characteristic Thermogravimetric analysis (TGA) profile of perampanel Form I.
Figure 19:
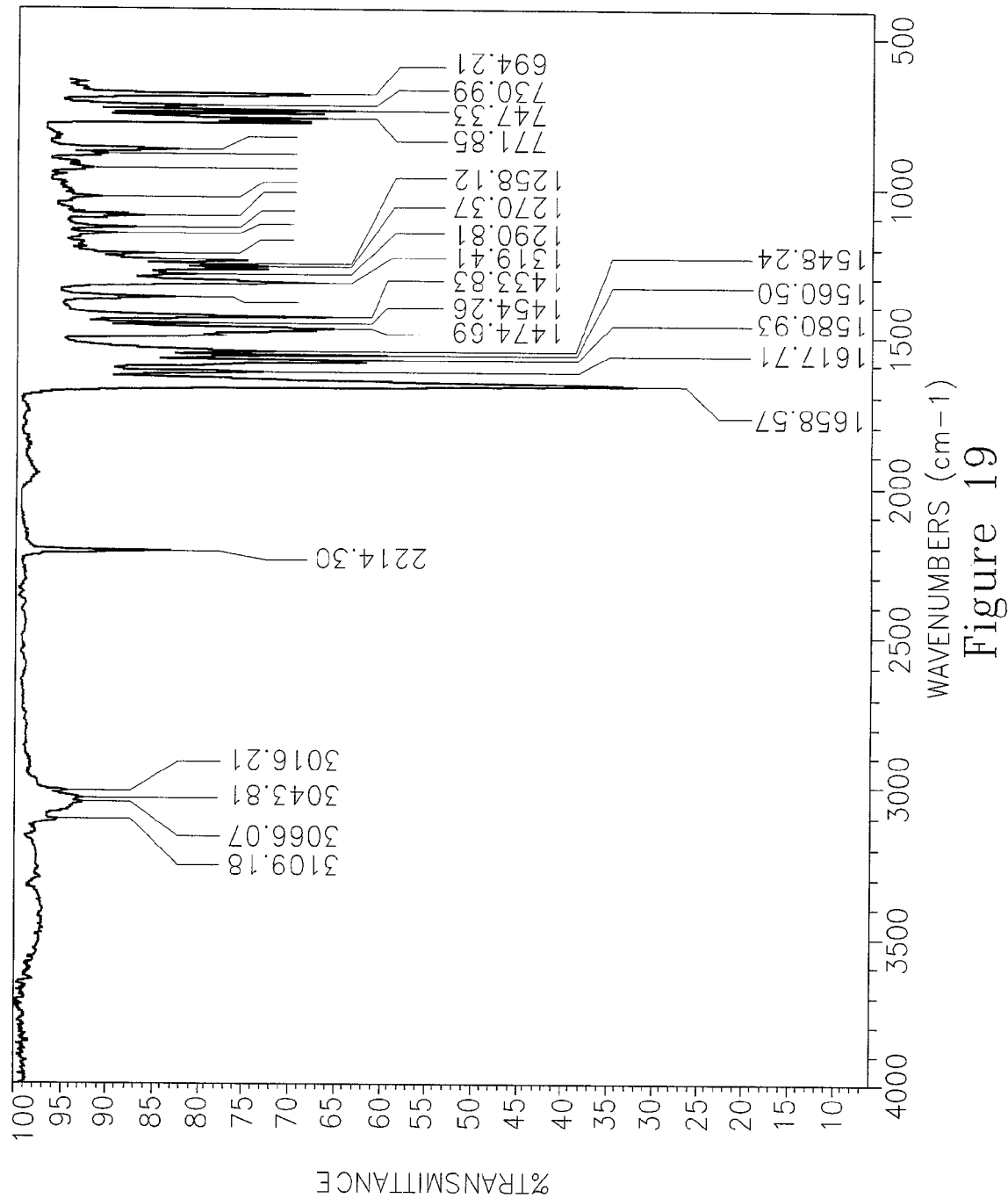
FIG. 19 illustrates a characteristic Fourier Transform Infrared (FTIR) spectrum of perampanel Form I.
Figure 20:
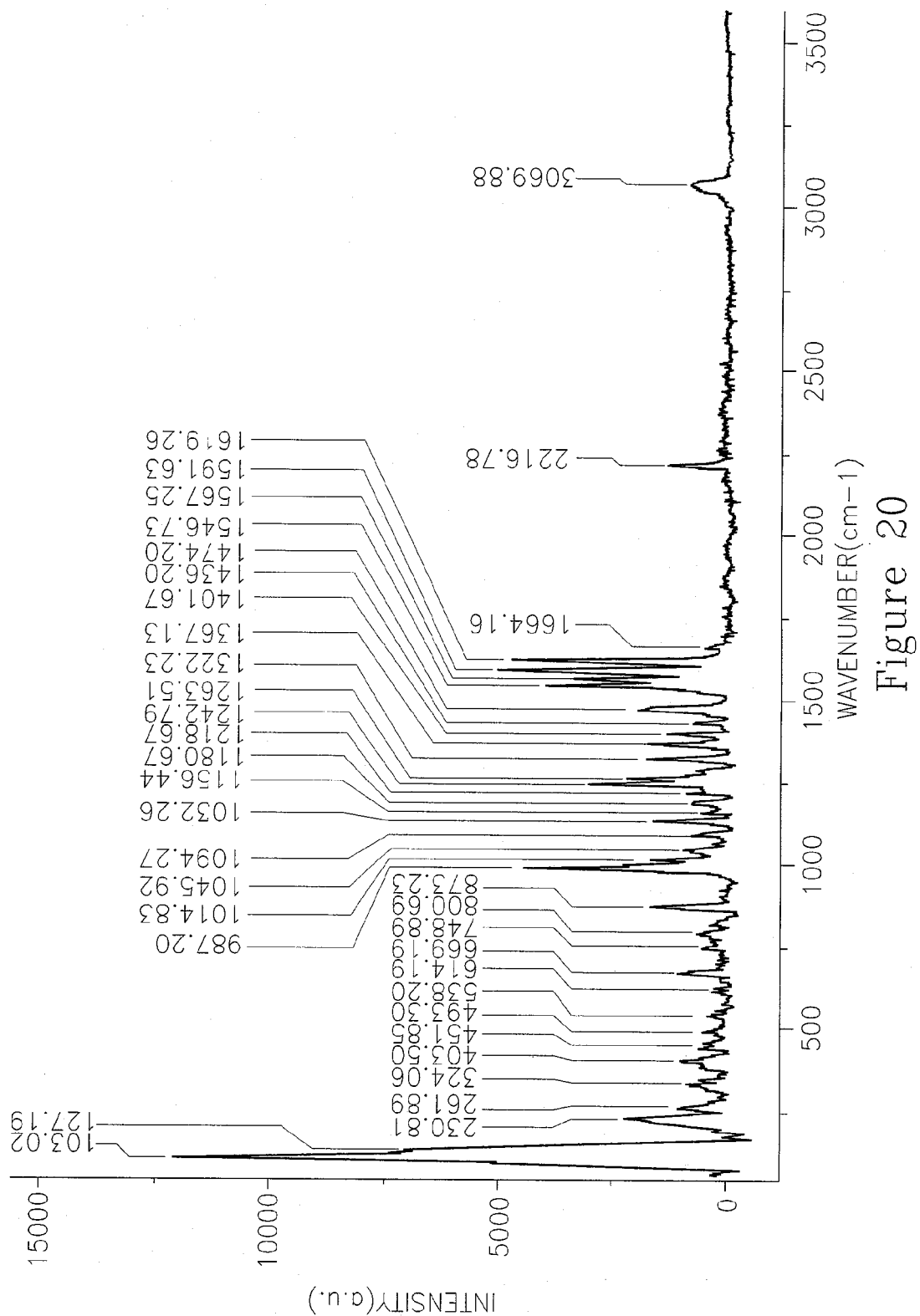
FIG. 20 illustrates a characteristic Fourier Transform-Raman (FT-Raman) spectrum of perampanel Form I.
Figure 21:
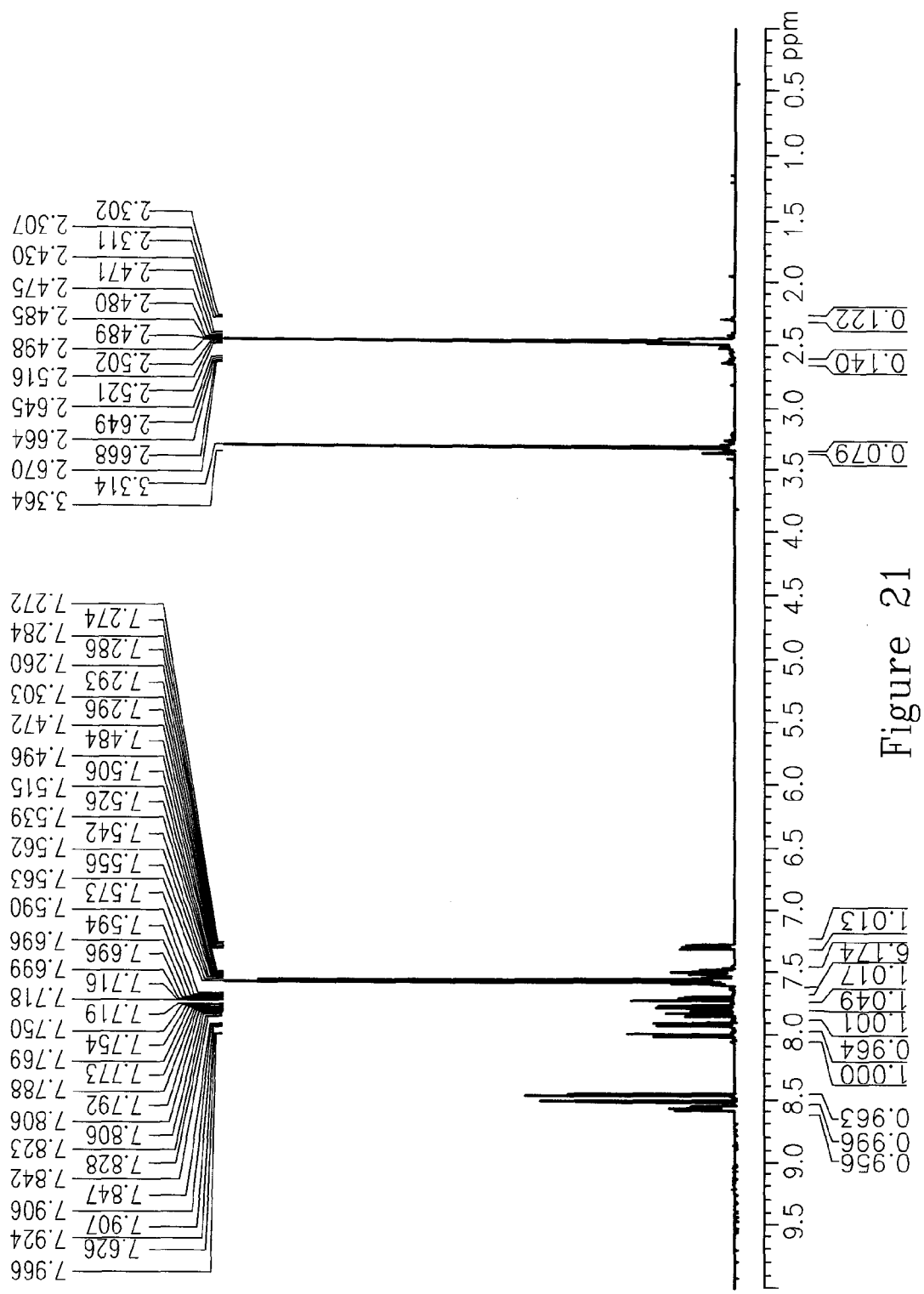
FIG. 21 illustrates a characteristic $^1$H-NMR spectrum of perampanel Form I.
Figure 22:
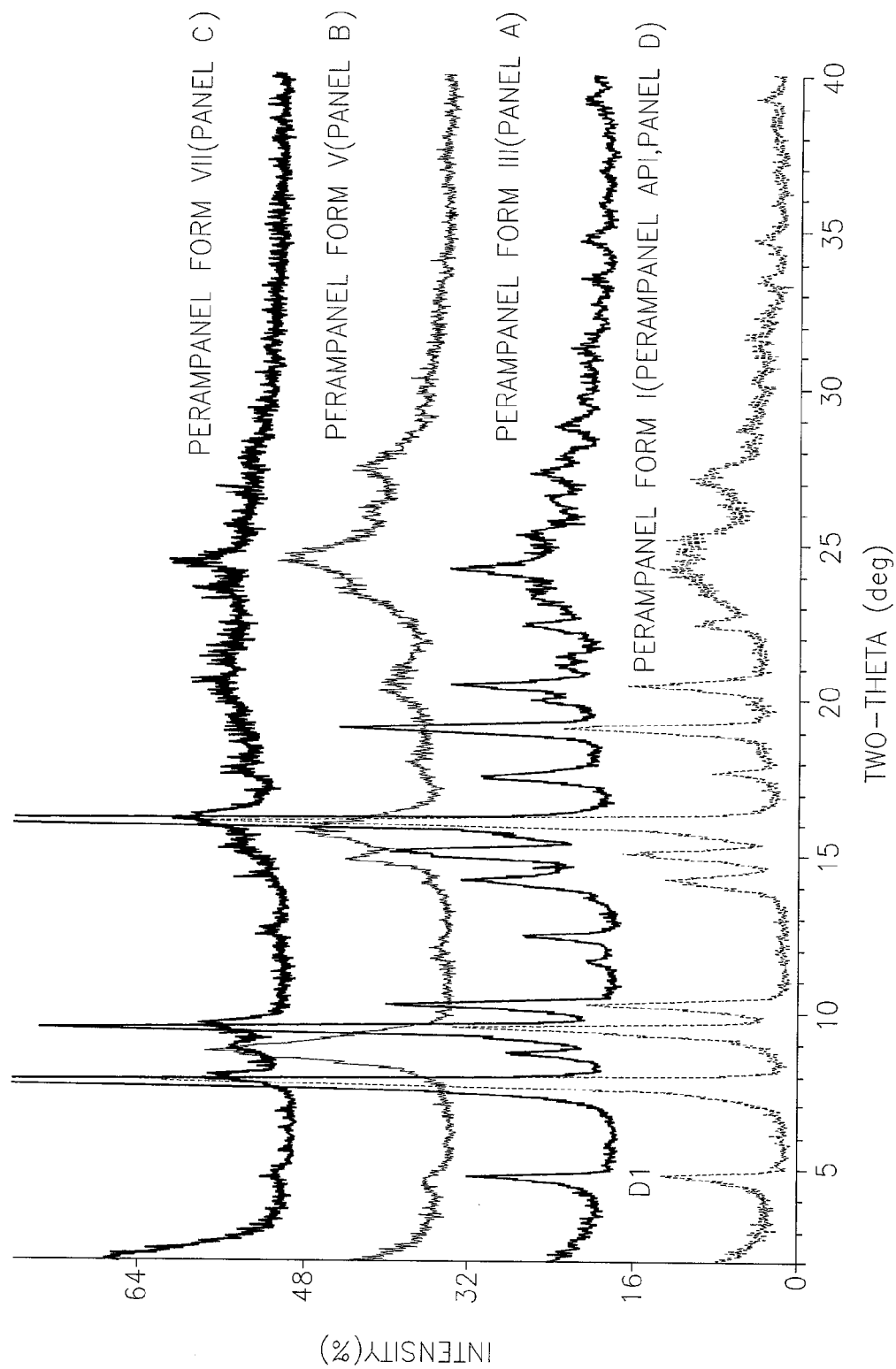
FIG. 22 illustrates a characteristic X-ray diffraction pattern of perampanel Forms III (panel A), V (panel B) and VII (panel C) of the present invention. Also shown for comparison is the X-ray diffraction pattern of crystalline perampanel Form I (perampanel API, panel D).

Perampanel Form I (WO 01/96308) (API) was characterized by an X-ray diffraction pattern (FIG. 16 and Table 4), DSC (FIG. 17), TGA (FIG. 18), FT-IR (FIG. 19), FT-Raman spectra (FIG. 20), and $^1$H-NMR (FIG. 21).

TABLE 4

Peak search report of XRPD of Form I

| No. | 2-Theta | Intensity (%) |
|---|---|---|
| 1 | 4.798 | 18.5 |
| 2 | 7.840 | 100.0 |
| 3 | 9.537 | 51.6 |
| 4 | 10.301 | 30.7 |
| 5 | 14.260 | 17.8 |
| 6 | 15.100 | 23.3 |
| 7 | 16.139 | 91.6 |
| 8 | 17.702 | 11.2 |
| 9 | 19.101 | 31.4 |

TABLE 4-continued

Peak search report of XRPD of Form I

| No. | 2-Theta | Intensity (%) |
|---|---|---|
| 10 | 20.460 | 20.7 |
| 11 | 22.401 | 8.4 |
| 12 | 24.238 | 15.5 |
| 13 | 25.300 | 13.0 |
| 14 | 27.118 | 11.3 |

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. An anhydrous crystalline form of perampanel (Form III) having an X-ray powder diffraction pattern with diffraction peaks at 2-theta values at about 8.7±0.1, 11.7±0.1, 12.5±0.1, and 20.0±0.1.

2. The crystalline perampanel (Form III) according to claim 1, having an X-ray powder diffraction pattern with diffraction peaks at 2-theta values at about 8.7±0.1, 11.7±0.1, 12.5±0.1, 20.0±0.1, 23.3±0.1, 26.4±0.1 and 28.7±0.1; or an X-ray powder diffraction pattern with diffraction peaks at 2-theta values at about 4.7±0.1, 7.8±0.1, 8.7±0.1, 9.5±0.1, 10.3±0.1, 11.7±0.1, 12.5±0.1, 14.2±0.1, 15.1±0.1, 16.1±0.1, 17.6±0.1, 19.1±0.1, 20.0±0.1, 20.5±0.1, 21.1±0.1, 21.4±0.1, 22.4±0.1, 23.3±0.1, 24.2±0.1, 25.3±0.1, 26.4±0.1, 27.2±0.1 and 28.7±0.1; or an X-ray diffraction (XRD) profile substantially as shown in FIG. 1 or in Table 1.

3. The crystalline perampanel (Form III) according to claim 1, further characterized by
   (i) a DSC profile substantially as shown in FIG. 2; or
   (ii) a TGA profile substantially as shown in FIG. 3; or
   (iii) an FT-IR spectrum substantially as shown in FIG. 4; wherein the IR spectrum comprises characteristic peaks at about 692±4, 733±4, 741±4, 783±4, 874±4, 938±4, 1033±4, 1067±4, 1132±4, 1147±4, 1185±4, 1219±4, 1246±4, 1261±4, 1276±4, 1314±4, 1368±4, 1432±4, 1455±4, 1470±4, 1550±4, 1569±4, 1588±4, 1622±4, 1656±4, 2214±4, 2351±4, 3012±4, 3050±4, 3118±4, and 3384±4 cm$^{-1}$; or
   (iv) a Raman spectrum substantially as shown in FIG. 5; wherein the Raman spectrum comprises characteristic peaks at about 117±4, 141±4, 179±4, 224±4, 255±4, 265±4, 303±4, 390±4, 448±4, 479±4, 545±4, 611±4, 663±4, 745±4, 783±4, 821±4, 866±4, 980±4, 1008±4, 1036±4, 1091±4, 1129±4, 1156±4, 1181±4, 1212±4, 1236±4, 1257±4, 1277±4, 1315±4, 1360±4, 1391±4, 1426±4, 1471±4, 1540±4, 1557±4, 1585±4, 1612±4, 1657±4, 2210±4, and 3066±4 cm$^{-1}$.

4. A pharmaceutical composition comprising as an active ingredient the crystalline perampanel (Form III) according to claim 1, and a pharmaceutically acceptable carrier.

5. A method of treating epilepsy or seizures comprising the step of administering to a subject in need thereof an effective amount of the crystalline perampanel (Form III) according to claim 1.

6. A process for preparing the crystalline perampanel (Form III) according to claim 1, the process comprising the steps of:
   (a) suspending perampanel in a solvent mixture comprising MEK:water, preferably at a ratio of about 1:1 (v/v) with stirring; and
   (b) isolating perampanel Form III.

7. A process for preparing the crystalline perampanel (Form III) according to claim 1, the process comprising the steps of:
   (a) dissolving perampanel in a solvent mixture comprising DCM:MTBE, preferably at a ratio of about 1:1 (v/v); and
   (b) evaporating the solvent so as to provide perampanel Form III;
wherein the evaporation in step (b) is optionally performed at about room temperature.

* * * * *